United States Patent
Kumar et al.

(10) Patent No.: US 11,435,344 B2
(45) Date of Patent: Sep. 6, 2022

(54) ELECTROCHEMICAL BIOSENSOR AND A METHOD OF SENSING ALBUMIN AND ITS COMPLEXES

(71) Applicant: INDIAN INSTITUTE OF SCIENCE, Bangalore (IN)

(72) Inventors: Vinay Kumar, Bangalore (IN); Navakanta Bhat, Bangalore (IN)

(73) Assignee: Indian Institute of Science, Bangalore (IN)

( * ) Notice: Subject to any disclaimer, the term of this patent is extended or adjusted under 35 U.S.C. 154(b) by 329 days.

(21) Appl. No.: 15/509,460

(22) PCT Filed: Sep. 1, 2015

(86) PCT No.: PCT/IB2015/056619
§ 371 (c)(1),
(2) Date: Mar. 7, 2017

(87) PCT Pub. No.: WO2016/038505
PCT Pub. Date: Mar. 17, 2016

(65) Prior Publication Data
US 2017/0241996 A1    Aug. 24, 2017

(30) Foreign Application Priority Data
Sep. 8, 2014   (IN) ........................... 4377/CHE/2014

(51) Int. Cl.
*G01N 33/68* (2006.01)
*G01N 27/327* (2006.01)
*G01N 33/543* (2006.01)

(52) U.S. Cl.
CPC ....... *G01N 33/5438* (2013.01); *G01N 27/327* (2013.01); *G01N 27/3277* (2013.01);
(Continued)

(58) Field of Classification Search
CPC ............ G01N 33/566; G01N 33/6827; G01N 33/5438; G01N 2333/76; G01N 2333/765;
(Continued)

(56) References Cited

U.S. PATENT DOCUMENTS

| 5,506,144 A * | 4/1996 | Sundrehagen ......... G01N 33/68 436/161 |
| 2004/0118704 A1* | 6/2004 | Wang ............... G01N 33/48785 205/792 |

(Continued)

OTHER PUBLICATIONS

International Search Report and Written Opinion of the International Searching Authority, Application PCT/IB2015/056619, completed Mar. 2, 2016, 12 pages.

*Primary Examiner* — Maris R Kessel
(74) *Attorney, Agent, or Firm* — Meunier Carlin & Curfman LLC

(57) ABSTRACT

An electrochemically active device for collecting and retaining a biological sample with a bioanalyte, the device provided with at least a two-electrode member and an albumin-binding and an electrochemically active receptor in chemical contact with the two-electrode members and the biological sample. The present invention also provides a point-of-care biosensor with the device of the present invention and a method for measuring a bioanalyte in a biological sample. The device, point-of-care biosensor and the method of the present invention facilitate accurate measurements concentrations of urine albumin, human serum albumin (HSA), glycated albumin (GA) and methemalbumin (MHA) by determining redox current values in reduced volumes of biological samples.

15 Claims, 29 Drawing Sheets

(52) U.S. Cl.
CPC ..... *G01N 33/6827* (2013.01); *G01N 2333/76* (2013.01); *G01N 2333/765* (2013.01)

(58) Field of Classification Search
CPC ................ G01N 27/48; G01N 27/26; G01N 27/327–3277; G01N 33/487; G01N 33/49; C12Q 1/00; C12Q 1/001; C12Q 1/004; C12Q 1/005; C12Q 1/006; C12Q 1/26–32; C12Q 1/34; C12Q 1/54; A61B 5/14532; A61B 5/14535; A61B 5/14536
See application file for complete search history.

(56) References Cited

U.S. PATENT DOCUMENTS

| | | | |
|---|---|---|---|
| 2005/0178674 A1* | 8/2005 | Hyland | G01N 27/3272 205/775 |
| 2005/0247573 A1 | 11/2005 | Nakamura et al. | |
| 2006/0191788 A1* | 8/2006 | Wayment | G01N 33/5438 204/403.01 |
| 2009/0246801 A1* | 10/2009 | Smith | G01N 33/54386 435/7.1 |
| 2009/0294304 A1* | 12/2009 | Hyland | G01N 33/683 205/792 |
| 2010/0089774 A1* | 4/2010 | Manohar | G01N 27/3271 205/792 |
| 2010/0267049 A1 | 10/2010 | Rutter | |
| 2010/0291611 A1 | 11/2010 | Bolbot et al. | |
| 2011/0053289 A1 | 3/2011 | Lowe et al. | |
| 2011/0269153 A1 | 11/2011 | Miller et al. | |
| 2012/0261257 A1 | 10/2012 | Vanjari et al. | |
| 2014/0273187 A1 | 9/2014 | Johnson et al. | |

\* cited by examiner

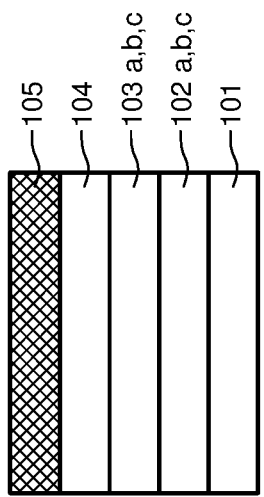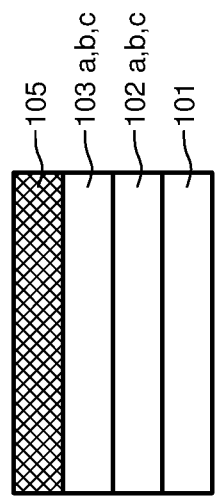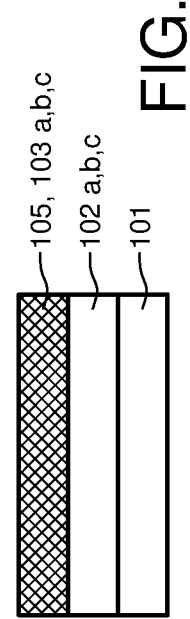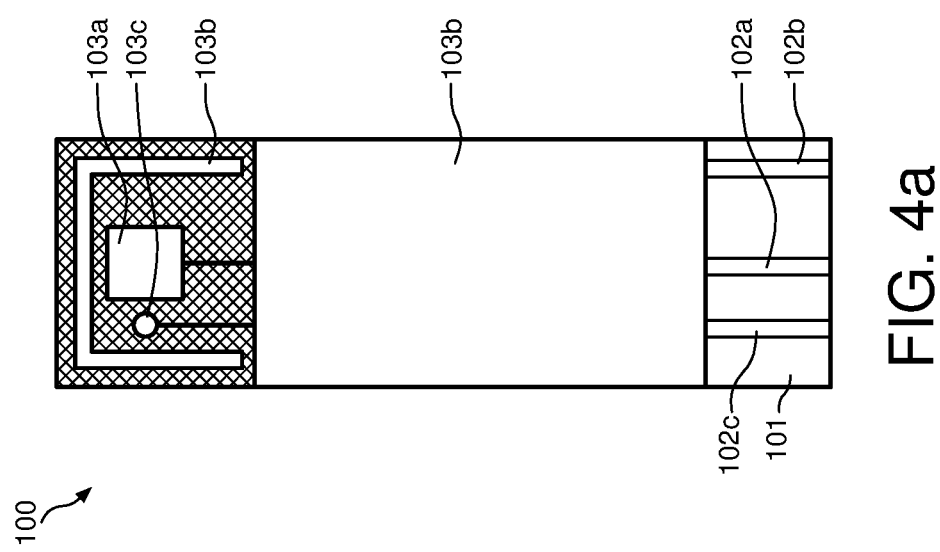

ELECTROCHEMICAL BIOSENSOR AND A METHOD OF SENSING ALBUMIN AND ITS COMPLEXES

FIELD OF INVENTION

This invention generally relates to biosensors and methods for quantitative measurement of bioanalytes in biological samples. More particularly, the present invention relates to an electrochemically active biosensor, for an accurate detection and quantitative measurement of albumin and its complexes, in biological samples of reduced volume.

BACKGROUND OF THE INVENTION

Albumin, which is a water-soluble globular protein, is the most abundant protein in the human blood. Human serum albumin, with the molecular weight 66,438 dalton, is synthesized in the liver and contains 585 amino acids. It comprises 60% of the total protein in blood plasma and provides 80% of osmotic pressure of blood. Albumin transports thyroid hormones, fatty acids, unconjugated bilirubin, hemin, drugs molecule and metal ions. Thus, it is called as molecular taxi inside the human body. Typical albumin concentration in the blood serum of adult human is 35-50 g/L.

Normal albumin level in the plasma has been recognized as a sign of good health. Human serum albumin (HSA) is either alone or an associative biomarker in several chronic diseases like necrosis, nephrosis, hepatitis, malnutrition, arthritis, immune disorders, cancer, diabetes and in some severe infections. Hypoalbuminemia, which is a deficit of albumin in blood, may be caused by liver disease, nephrotic syndrome, excess loss in bowel and increased vascular permeability. Whereas, Hyperalbuminemia is a sign of severe dehydration, in a human body.

Urine albumin is a potential biomarker for diabetic nephropathy. Diabetes is a chronic metabolic disease and affects almost every vital body part like the heart, brain, kidney, eye and nervous system. Diabetic nephropathy is a primary cause of kidney failure worldwide. Diabetic nephropathy is the progressive kidney disease caused by the damage of blood capillaries in the kidney glomeruli. Albumin is the blood component and a healthy kidney doesn't allow its excretion in the urine, because of the molecular size of albumin and the negative electric charge at glomerulus. The presence of albumin in urine is a well-established biomarker for the early detection of diabetic nephropathy. For a healthy person urine albumin should be less than 30 mg/L. If urine albumin is in between 30-300 mg/L then this condition is called as microalbuminuria. According to American diabetes association, annual screening of microalbuminuria is mandatory for type-2 diabetic patients from the time of diagnosis and for type-1 diabetic patients after 5-years of diagnosis.

Since the albumin production occurs in liver, thus serum albumin is an important biomarker in the liver function tests. In most patients with acute hepatitis, or cirrhosis, the albumin level is nearly 30 g/L while with toxic hepatitis or hepatic tumors it drops to 25 g/L.

Albumin plays a vital role in health and diseases. There are thousands of applications for serum albumin covering a wide range of physiological conditions.

Protein glycation is now a well-known marker for the progress of diabetes complications and to understand the cause of other serious complications arising out of protein glycation. Glycated hemoglobin is a gold standard for long-term diabetes management, which gives the average blood glucose of 90-120 days. Albumin is a protein without prosthetic group and additives. During circulation, albumin accumulates glucose through non-enzymatic glycosylation. Glycated albumin can be used as a marker for glycemic control. Half-life of albumin is significantly lower compared to the life span of RBC, thus glycated albumin can be used as an intermediate glycemic indicator. Monthly assessment of glycated albumin in patients of diabetes more than 5 years can be useful in the prevention of diabetes complications. Glycated albumin test is useful in anemic and hemoglobinopathies patients for whom the clinically measured HbAlc level may be inaccurate.

Methemalbumin is important in the diagnosis of acute hemorrhagic pancreatitis. Studies show linkage of elevated levels of methemalbumin level with hemorrhagic pancreatitis, thus providing a good index for the diagnosis of this disease.

Electrochemical sensing of albumin is comparatively more challenging than the sensing of metalloproteins. Metalloproteins, such as hemoglobin and myoglobin contain iron Fe (II) redox center, in the form of heme prosthetic group and thus it is relatively easy for the protein molecule to communicate with the electrode surface. On the other hand, albumin doesn't contain any heme prosthetic group in its structure, so ideally there is no possibility of electron communication between the protein molecule and the electrode surface.

Electrochemical sensors, to sense bioanalytes are used in a wide number of specialized sensor applications, to quantitatively sense and measure albumin proteins in biological samples. Typical electrochemical sensors include one or more thin conductors applied by thin film deposition processes and subsequently patterned by photolithographic mask and/or etch techniques in combination with layers of nonconductive film materials but instead of using these techniques, screen printing is a good choice of low cost electrochemical bio-sensors. However, known devices and methods are either based on immunological techniques or complex electrode modification, which is not suitable for a low cost point-of-care biosensor.

J. Micromech Microeng 17 (2007) 835-842 by Chao-June Huang et al., discloses an electrochemical sensing of urine albumin, to measure the concentration of urine albumin, where the adsorption of albumin on the surface of a gold electrode due to the sulfur-gold bond formation.

"Development of polypyrrole-based human serum albumin sensor" by Richard et al., in J. Analytica Chemica Acta (1921), discloses an electro synthetic method, which is suitable for direct incorporation of antibodies into conducting polymeric coatings.

EP2040074 discloses a colorimetric method for assaying urine albumin by using a protein assay indicator containing a halogenated xanthene-based dye.

U.S. Ser. No. 00/518,2214 discloses a fluorescence-based method for the detection of serum albumin. The method is based on the fluorescence of anionic cyanine dye, which is intensified in the presence of serum albumin.

US2006/0223192 A1 discloses immune-chromatographic assay system for measuring the amount of glycated albumin in a blood sample relative to the total level of albumin in a sample.

EP0769697 discloses a colorimetric dry test apparatus for determining glycated albumin using a reagent layer containing an albumin-staining dye and a glycated albumin-staining dye.

EP1810036 discloses a test strip for semi-quantitatively measuring the amount of albumin in a urine sample. The test strip contains Coomassie Brilliant Blue on a test pad area, which is wetted with the urine sample, providing a color change in the presence of protein.

US2005/22339215 discloses monoclonal antibodies and hybridomas based method for glycated albumin detection.

J. Clin. Chem. 21/10, 1506-1510 (1975) by Scot N Andres discloses the methemalbumin detection using diethylaminoethyl Sephadex ion-exchange chromatography.

US2014/0170766 A1 discloses a point-of-care device for measuring the glycated albumin as compared to the total albumin in a saliva sample using photometric method based on aptamer receptors.

These disclosed methods are primarily based on anti-albumin antibody binding, change in redox current based on adsorption of albumin at electrode surface and microfluidics.

Various point-of-care devices are also available for albumin detection like Hemoclue's Albumin 201, Axis shield's ACR and Siemens's DCA-Vantage.

All these known devices and methods are either based on immunological techniques or involving complex electrode modifications.

Objects of the Present Invention

The primary object of the present invention is to provide an electrochemically active and albumin-binding device, for collection and retention of biological samples, for a subsequent quantitative detection of albumin and its complexes, particularly, urine albumin, human serum albumin (HSA), glycated albumin (GA), and methemalbumin (MHA), in biological samples of reduced volume.

An object of the present invention to provide a device holder, adapted to receive the electrochemically-active and albumin-binding device.

Another object of the present invention to provide a point-of-care biosensor, adapted to receive the electrochemically-active and albumin binding device, for the detection and quantitative measurement of urine albumin, human serum albumin (HSA), glycated albumin (GA), and methemalbumin (MHA), in biological samples of reduced volume, through a measurement of redox current flowing through the electrochemically active device, on the application of an electric potential.

It is also an object of the present invention to provide a method for the detection and quantitative measurement of urine albumin, human serum albumin (HSA), glycated albumin (GA), and methemalbumin (MHA), through an accurate measurement redox current flowing through the electrochemically-active and albumin binding devices.

It is also an object of the present invention to provide a method for the quantitative measurement of GA, which is a known electrically-insulated biomolecule without any metallic prosthetic group.

SUMMARY OF THE PRESENT INVENTION

The present invention provides an electrochemically active device for collecting and retaining a biological sample with at least a two-electrode member and an albumin binding and an electrochemically active receptor in chemical contact with the two-electrode members. The present invention also provides a point-of-care biosensor with device of the present invention and method of measuring a bioanalyte in a biological sample. The device, point-of-care biosensor and the method of the present invention facilitate accurate measurements concentrations of albumin bioanalytes by determining redox current values in the urine and blood samples.

BRIEF DESCRIPTION OF THE DRAWINGS

FIG. 4 (a) is schematic top view of the electrochemically active and albumin-binding device with a three-electrode arrangement for urine albumin and human serum albumin.

FIG. 4(b) is a cross-sectional view of the electrochemically active and albumin-binding device, where the receptor is arranged on the surface of the membrane.

FIG. 4(c) is a cross-sectional view of the electrochemically active and albumin-binding device, where the receptor is arranged on the surface of the electrode.

FIG. 4(d) is a cross-sectional view of the electrochemically active and albumin-binding device, where the electrode acts as a receptor.

FIG. 23(a) depicts reduction and oxidation currents plot versus urine albumin concentration

DETAILED DESCRIPTION OF THE INVENTION

Figure 1:
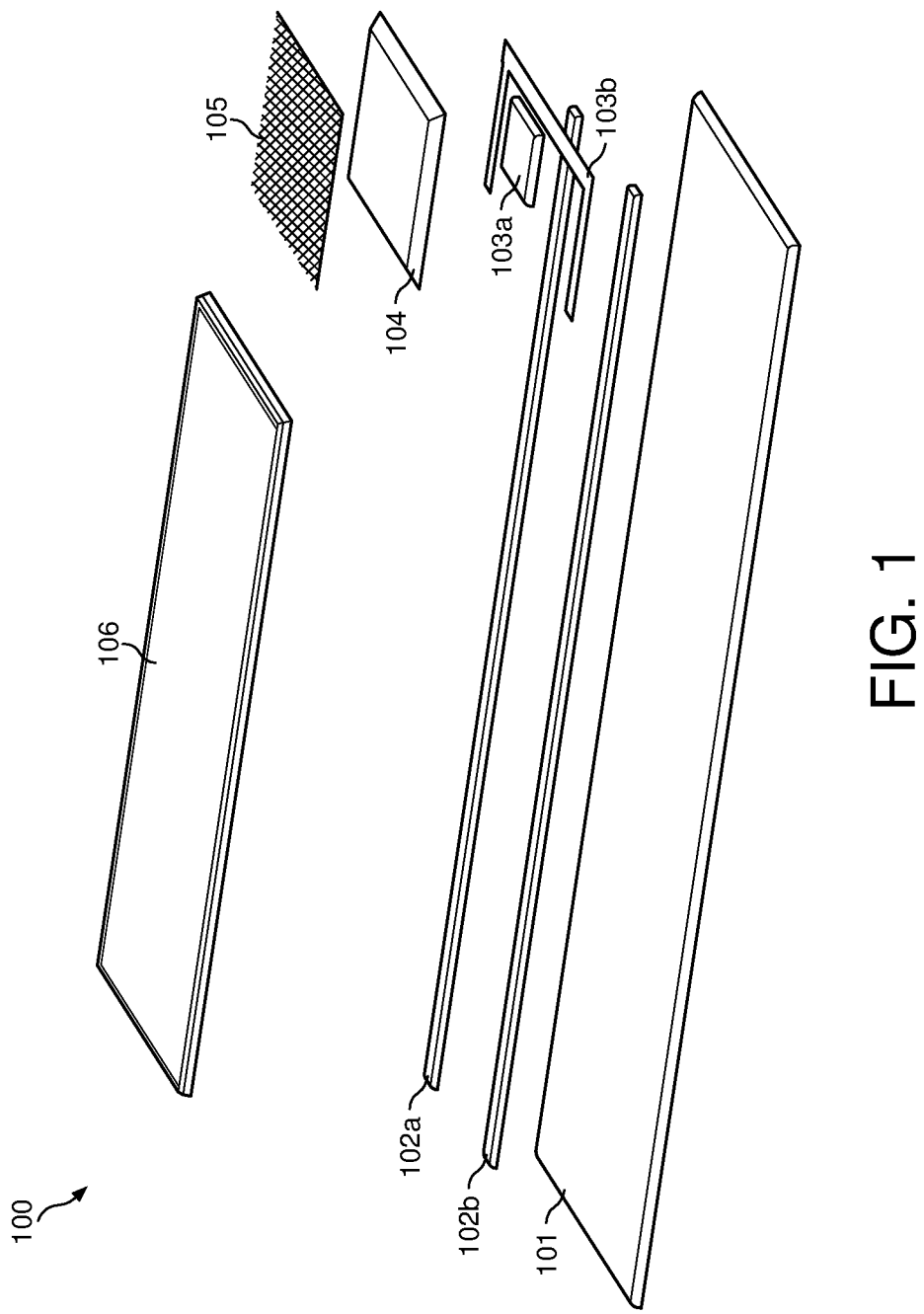
FIG. 1 is a schematic exploded view of the electrochemically active device and albumin-binding device, depicting a two-electrode arrangement, in accordance with an aspect of the present invention.

Accordingly, the present invention provides an albumin-binding and an electrochemically active biosensor, for an accurate detection and quantitative measurement of albumin and its complexes such as bioanalytes such as urine albumin, human serum albumin (HSA), glycated albumin (GA), and methemalbumin (MHA), in reduced volumes of biological samples of urine and blood.

In an aspect of the present invention an electrochemically active device for collecting and retaining a biological sample is provided with at least a pair of conductive tracks disposed on a substrate and the conductive tracks are connected to at least a two-electrode member. The electrode member is in chemical contact with the electrode member and a biological sample having a bioanalyte. The device of the present invention is advantageously provided with housing in the form of a cartridge or a cassette.

In another aspect of the present invention a holder for holding the electrochemically active device of the present invention is provided with housing having at least a device detection and signal conditioning arrangement disposed in a housing. A connector, preferably, a USB connector is provided at one end of the housing and an electrically conductive port arranged at the other end of the housing. The electrochemically-active device is arranged to connect to the housing through the electrically conductive port for collecting and retaining a biological sample. The device is provided with at least a pair of conductive tracks, at least a two-electrode member and an albumin-binding and an electrochemically active receptor arranged on a substrate. The receptor is arranged to be in chemical contact with the two-electrode member and the biological sample containing the bioanalyte to be measured.

In yet another aspect of the present invention a point-of-care biosensor for measuring a concentration of a bioanalyte in a biological sample is provided with a housing having a display member and an electrically conducting port. An electrochemically-active device is connected to the housing through the electrically conductive port for collecting and retaining a biological sample. The device is provided with at least a pair of conductive tracks, at least a two-electrode member and an albumin-binding and an electrochemically active receptor arranged on a substrate. The receptor is in chemical contact with the two-electrode member and the biological sample with a bioanalyte. A digital controller is arranged in the housing and configured to measure redox current from a redox potential applied to the device, retrieve and display albumin bioanalyte concentration, by measuring a corresponding redox current linearly matching it to the albumin concentration.

It is also an aspect of the present where a method for measuring a concentration of albumin bioanalyte and its complexes in a biological sample is provided. In this method a redox potential is applied to at least a two-electrode member, which is in chemical contact with an electrochemically active and an albumin binding receptor, loaded with a reduced volume of a biological sample with a bioanalyte. In the method, a concentration of the albumin bioanalyte is measured in the biological sample by linearly matching with a corresponding redox current of the two-electrode member.

Now, the preferred embodiments of the invention are described by referring to the accompanied illustrative drawings. Initially, the preferred embodiments of an electrochemically active device of the present invention, for collecting and retaining a biological sample, for a subsequent measurement of the desired albumin analyte and its complexes present in the biological sample, are described by referring to FIG. 1.

The device 100 as shown in FIG. 1 is provided with a substrate 101, which acts as a base on which other constituents of the device are constructed or arranged. The substrate 101, in this embodiment is exemplarily shown as an elongated rectangular structure. However, it is understood here that the substrate 101 can take other shapes such as square, circular depending on the shape and configuration of a biosensor that holds the device 100. The substrate 101 can be made of any suitable rigid or flexible material that is suitable for the incorporation of patterned electrodes. For instance, materials such as polyvinylchloride (PVC), polyethylene terephthalate (PET), polymethylmethacrylate (PMMA), epoxy fiber composites, polyamides composites, and paper can be used as preferred materials for the substrate 101. Whereas, the preferred rigid materials for the substrate 101 can be ceramic, glass or any other like materials. In any case, the selection of suitable material for the substrate 101 is made to ensure that the substrate 101 can not only provide a desirable strength and flexibility but also can act as an electrical insulator. Advantageously the substrate 101, considering the applications of the invention, is hydrophilic in nature to prevent percolation of the biological sample, when it comes in physical contact with the substrate 101. The surface of the substrate 101 is generally provided with a smooth texture. However, the substrate 101 can also be provided with a rough surface and/or with cavities or wells. The edges of the substrate 101 are also provided with suitable profiles, such as tapered or curved, to facilitate an easy ingress into and egress out of a biosensor that is used for the measurement of the bioanalyte.

A pair of conductive tracks 102a and 102b are arranged on the substrate 101. The conductive tracks 102a and 102b are formed by using any patterning method such as screen printing, lithography, thermal evaporation, sputtering, laser patterning, preferably screen-printing. In an exemplary aspect, in FIG. 1, pair of conductive tracks 102a and 102b are formed for implementation. However, the required number of conductive tracks can be suitably increased or varied. The routing of the conductive tracks 102a and 102b are exemplarily shown as straight tracks in FIG. 1. Other suitable configurations for the conducting tracks such as polygons can be used. The material for the conductive tracks 102a and 102b can be an electrically conductive materials such as copper, aluminum, gold, silver, platinum, carbon, or any other suitable electrically conducting material or alloys of these materials. The material for the conducting tracks 102a and 102b can also be electrochemically active such as gold, platinum, mercury, carbon, glassy carbon and graphite. The conducting tracks 102a and 102b are used to establish an electrical connection with the biosensor of the present invention as hereinafter described.

Pair of electrodes 103a and 103b are electrically connected to the conducting tracks 102a and 102b respectively, as shown in FIG. 1. The electrodes 103a and 103b are overlaid on the conducting tracks 102a and 102b and arranged at the terminal ends of the conducting tracks 102a and 102b, so as to form a layer above the conducting tracks 102a and 102b, as shown in FIG. 1. The material for the electrodes 103a and 103b are selected from metals or alloys, which are electrochemically active, such as gold, platinum, mercury, carbon, glassy carbon and graphite. In the arrangement of electrodes as shown in FIG. 1, the electrode 103a acts as a working electrode and whereas the electrode 103b is a counter electrode.

A membrane 104 is arranged on the pair of electrodes 103a and 103b as shown in FIG. 1, which acts a base member for the integration of a receptor as hereinafter described. The material for the membrane 104 can be polymer, cellulose, nitrocellulose, nylon, cotton fabric, filter paper etc. The membrane 104 is treated with a boronate affinity agent, selected from the group consisting of boronic acid, phenyl boronic acid (PBA), aminophenyl boronic acid (APBA) and derivatives thereof, preferably aminophenyl boronic acid (APBA). The membrane is treated with the boronate affinity agent for sensing glycated albumin.

The device 100 of present invention is used for the detection and quantitative measurement of albumin bioanalytes such as urine albumin, human serum albumin (HSA), glycated albumin (GA) and methemalbumin (MHA), either individually or in combination, in human biological samples. Accordingly, in the present invention an albumin binding and an electrochemically active receptor 105 is in chemical contact with the electrodes. The receptor 105, in this preferred embodiment, is shown as a layer of electrochemically active substance. The electrochemically active substance that is used as a receptor 105, to detect urine albumin in a urine biological sample and serum albumin (SA) in a biological blood sample, is at least an organic, inorganic, metal porphyrin substance, preferably, hemin, hematin, alkaline hemin or alkaline hematin, copper chloride ($CuCl_2$), a salt of copper (Cu(II)), methylene blue, a combination of methylene blue and hemin, hematin, alkaline hemin or alkaline hematin, a combination of methylene blue and a salt of copper (Cu(II)) and other variants thereof.

The initiation of chemical contact of the receptor 105 with the electrodes 103a and 103b is preferably performed in the following manner. A solution of receptor 105 is prepared and dispensed on the electrodes and dried to form a solid chemical layer on the electrodes 103a and 103b and such a functionalized electrode is used for the quantitative measurement of the bioanalyte.

Alternately, the receptor solution is pre-mixed with a selected biological sample containing the desired bioanalyte and a reduced volume of the pre-mixed solution is dispensed on the electrodes 103a and 103, which are optionally provided membrane 104.

In another aspect of the present invention, the receptor solution is prepared separately and dispensed directly on the electrode or the membrane arranged on the electrode. Thereafter, the desired biological sample having albumin bioanalyte is applied on the electrode.

A passivation layer 106 is arranged to cover the conductive tracks as shown in FIG. 1. The passivation layer 106 is used to provide protection for the conductive elements of the device and to precisely define the electrode region.

Figure 2:
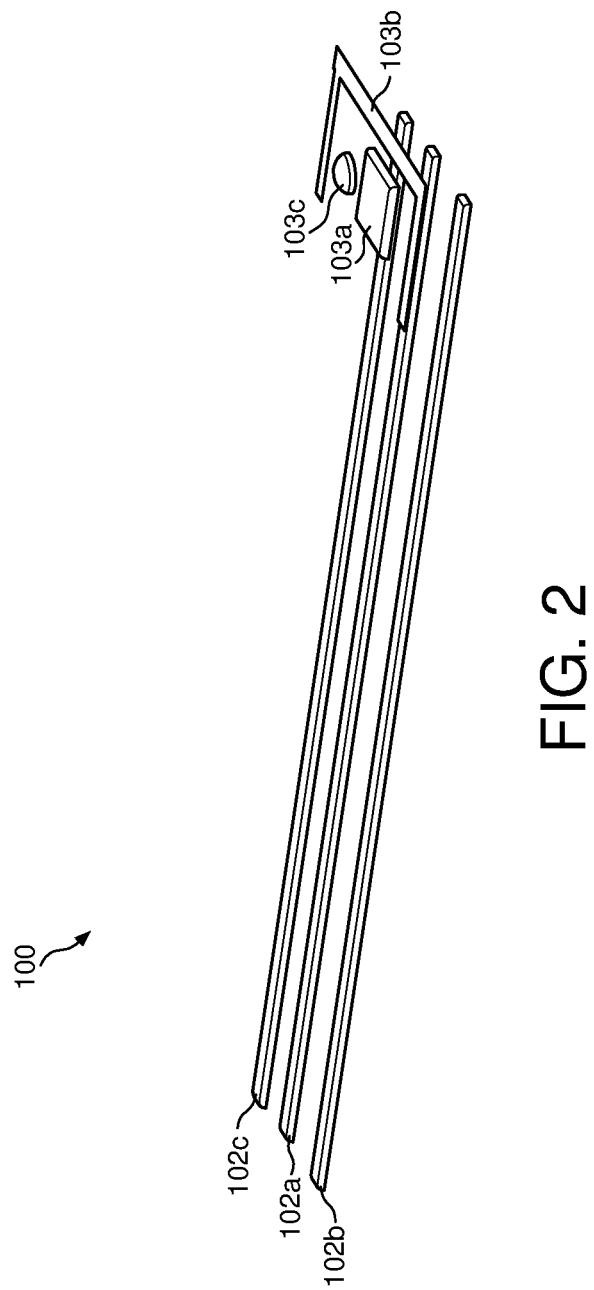
FIG. 2 is a schematic exploded view of a three-electrode arrangement, of the electrochemically active and albumin-binding device, in accordance with another aspect of the present invention.

In yet another aspect of the present invention, as shown in FIG. 2, the device 100 of the present invention is shown with an arrangement of set of three electrodes 103a, 103b and 103c is implemented in conjunction with a receptor (as shown in FIG. 1), where the electrodes 103a, 103b and 103c are connected to the conducting tracks 102a, 102b and 102c respectively, to collect and retain a biological sample. The increased number of electrodes facilitates the detection of a single bio-analyte in the biological sample with an increased accuracy. In this implementation the electrode 103c acts as a reference electrode. The preferred material for the reference electrode 103c is silver (Ag), a silver chloride (AgCl), silver/silver chloride (Ag/AgCl) or saturated calomel, where the potential of the electrodes does not change with time.

Figure 3A:
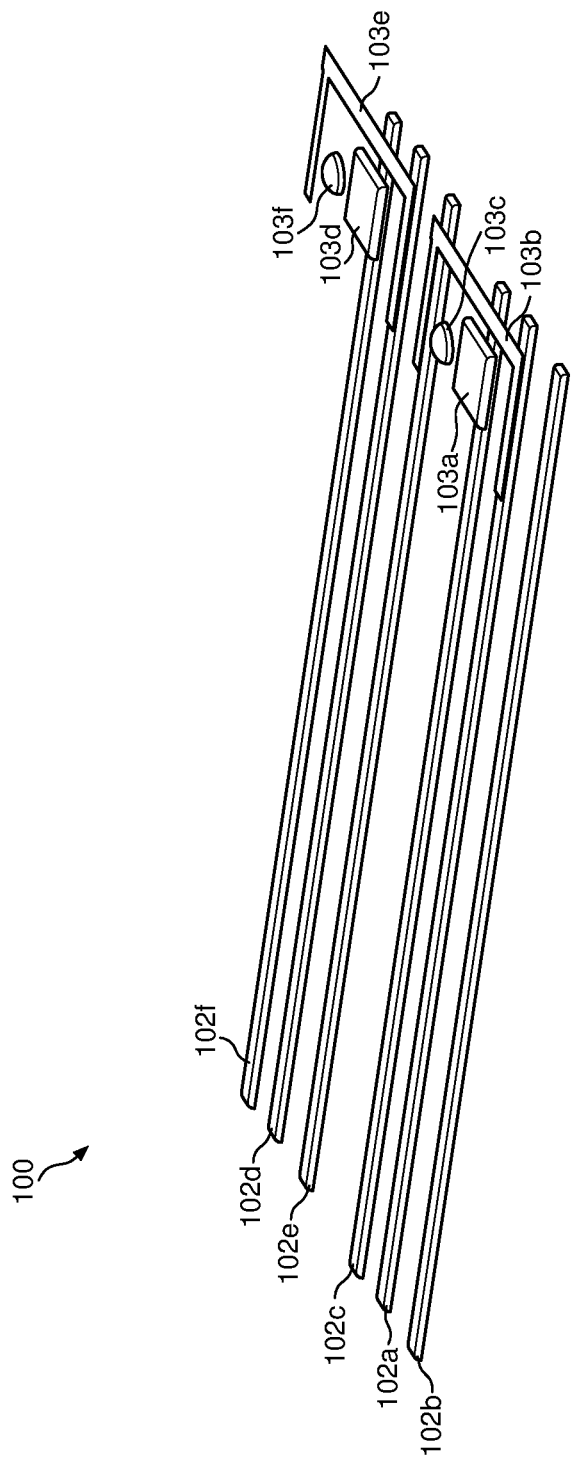
FIG. 3(a) is a schematic exploded view of two pairs of three-electrode arrangement, of the electrochemically active and albumin-binding device, in accordance with yet another aspect of the present invention.
Figure 3B:
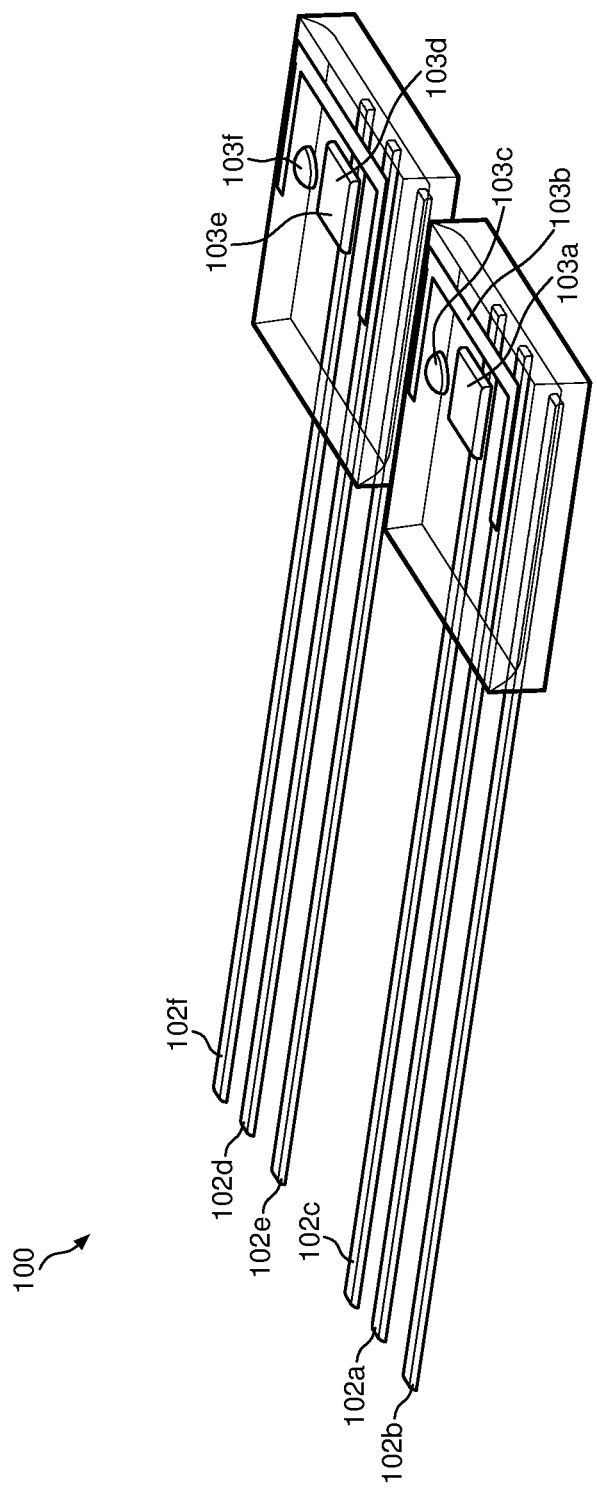
FIG. 3(b) is a schematic exploded view of two pairs of three-electrode arrangement with trays, of the electrochemically active and albumin-binding device, in accordance with yet another aspect of the present invention.

In yet another aspect of the present invention as shown in FIG. 3(a), the device 100 of the present invention is shown with two pairs of three-electrodes 103a, 103b, 103c, 103d, 103e and 103f are arranged on the conducting tracks 102a, 102b, 102c, 102d, 102e and 102f and are adapted for use to measure the concentration of multiple bio-analytes, in given biological samples. In this aspect, in case, the desired biological samples are blood and urine, shielded wells or trays are arranged on the electrodes, to demarcate two different sensing areas, as shown in FIG. 3(b), to facilitate an independent sensing of the biological samples. Accordingly, two separate receptors are provided in conjunction with each of the pair of the electrodes to receive these samples and separate measurement of concentrations of albumin in these two different biological samples is performed. In addition, if deemed necessary, physical partitions as illustrated in FIG. 3(b) may be provided to separate the electrodes.

As shown in FIG. 4(a), which illustrates a three-electrode arrangement of a device 100 for the measurement of microalbuminuria and HSA, by adopting receptors selected from at least an organic, inorganic, metal porphyrin substance, preferably, hemin, alkaline hemin, alkaline hematin, copper chloride (CuCl$_2$), a salt of copper (Cu(II)), methylene blue, methylene blue and hemin, hematin, alkaline hemin or alkaline hematin, a combination of methylene blue and a salt of copper (Cu(II)).

FIG. 4(b), which is a corresponding cross-sectional view depicts a substrate 101 on the surface of which conducting tracks 102a, 102b, 102c are arranged. A 3-electrode arrangement with a working electrode 103a, counter electrode 103b and reference electrode 103c connected to the conducting tracks 102a, 102b, 102c. The membrane 104 is arranged on surface of the electrodes 103a, 103b and 103c. The receptor layer 105 is arranged on the surface of the membrane 104.

FIG. 4(c), which is a corresponding cross-sectional view depicting a substrate 101 on the surface of which conducting tracks 102a, 102b, 102c are arranged. A 3-electrode arrangement with a working electrode 103a, counter electrode 103b and reference electrode 103c connected to the conducting tracks 102a, 102b, 102c. The receptor 105 is arranged on surface of the electrodes 103a, 103b and 103c.

FIG. 4(d), which is a corresponding cross-sectional view depicting a substrate 101 on the surface of which conducting tracks 102a, 102b, 102c are arranged. A 3-electrode arrangement with a working electrode 103a, counter electrode 103b and reference electrode 103c connected to the conducting tracks 102a, 102b, 102c, where the electrodes are treated with the receptor 105.

The embodiments as shown in FIGS. 4(a) (b), (c) and (d) are used to measure albumin bioanalyte in urine and blood samples.

Figure 5B:
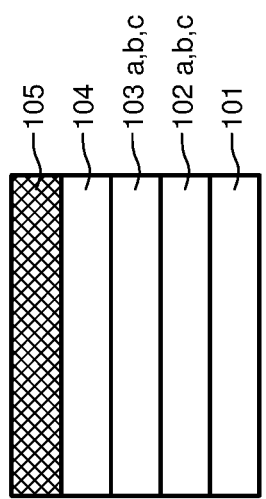
FIG. 5(b) is a cross-sectional view of the electrochemically active and albumin-binding device, where the receptor is arranged on the surface of the membrane.
Figure 5C:
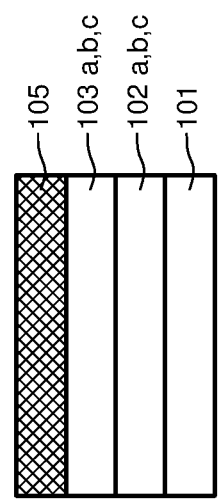
FIG. 5(c) is a cross-sectional view of the electrochemically active and albumin-binding device, where the receptor is arranged on the surface of the electrode.
Figure 5A:
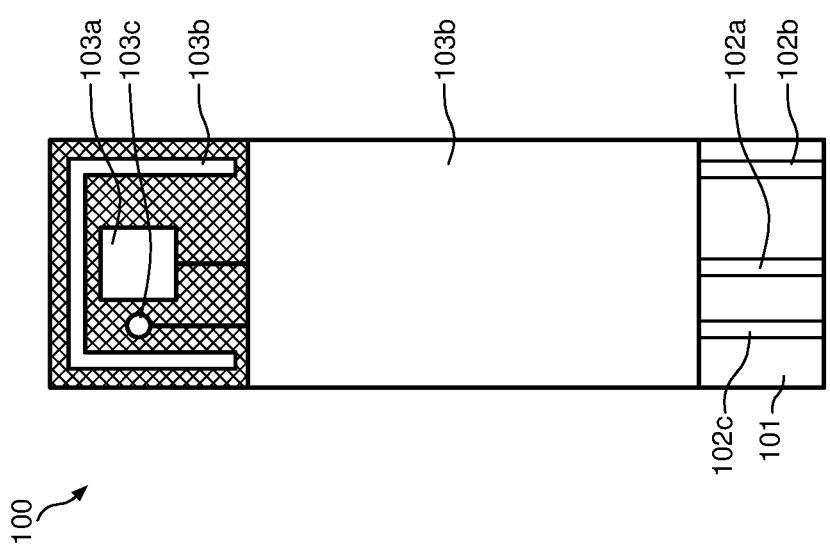
FIG. 5 (a) is schematic top view of the electrochemically active and albumin-binding device with a three-electrode arrangement for methemalbumin.

As shown in FIG. 5(a), depicts an illustration of a three-electrode arrangement of the device 100, to measure methemalbumin complex in biological samples, using methylene blue (MB) as receptor.

FIG. 5(b), which is a corresponding cross-sectional view depicting a substrate 101 on the surface of which conducting tracks 102a, 102b, 102c are arranged. A 3-electrode arrangement with a working electrode 103a, counter electrode 103b and reference electrode 103c connected to the conducting tracks 102a, 102b, 102c. The membrane 104 is arranged on surface of the electrodes 103a, 103b and 103c. The receptor layer 105 is arranged on the surface of the membrane 104.

FIG. 5(c), which is a corresponding cross-sectional view depicting a substrate 101 on the surface of which conducting tracks 102a, 102b, 102c are arranged. A 3-electrode arrangement with a working electrode 103a, counter electrode 103b and reference electrode 103c connected to the conducting tracks 102a, 102b, 102c. The receptor 105 is arranged on surface of the electrodes 103a, 103b and 103c.

The embodiments as shown in FIGS. 5(a),(b) and (c) are used to measure methemalbumin complex in biological samples.

Figure 6A:
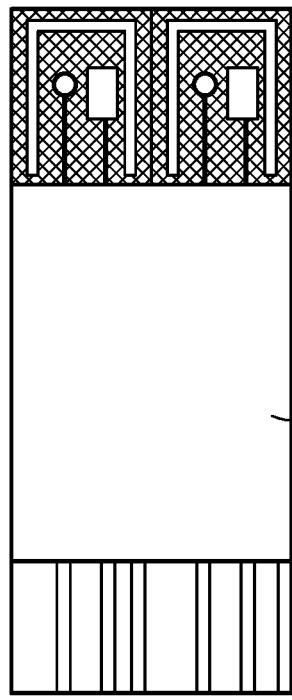
FIG. 6(a) is schematic top view of the electrochemically active and albumin-binding device with two sets of a three-electrode arrangement for quantitative measurement of glycated albumin.

As shown in FIG. 6(a), depicts a top view of the electrochemically active and albumin-binding device 100 with two sets of three electrodes, for the measurement of total albumin and glycated albumin in biological samples.

Figure 6B:
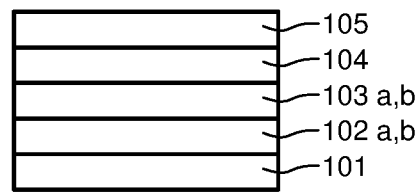
FIG. 6(b) is a cross-sectional view of the electrochemically active and albumin-binding device, where the receptor is arranged on the surface of the membrane for total human serum albumin detection.

FIG. 6(b), which is a corresponding cross-sectional view depicting a substrate 101 on the surface of which conducting tracks 102a, 102b, 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b, 102c. The membrane 104 is arranged on surface of the electrodes 103a, 103b and 103c. The receptor layer 105 is arranged on the surface of the membrane 104.

Figure 6C:
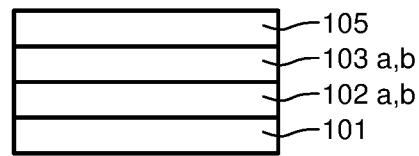
FIG. 6(c) is a cross-sectional view of the electrochemically active and albumin-binding device, where the receptor is arranged on the surface of the electrode for total human serum albumin detection.

FIG. 6(c), which is a corresponding cross-sectional view depicting a substrate 101 on the surface of which conducting tracks 102a, 102b, 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b, 102c. The receptor 105 is arranged on surface of the electrodes 103a, 103b and 103c.

Figure 6D:
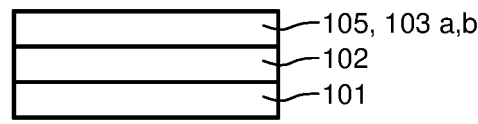
FIG. 6(d) is a cross-sectional view of the electrochemically active and albumin-binding device, where the electrode acts as a receptor for total human serum albumin detection.

FIG. 6(d), which is a corresponding cross-sectional view depicting a substrate 101 on the surface of which the conducting tracks 102a, 102b, 102c are arranged in the left half portion of the substrate 101. A 3-electrode arrangement in the left half portion of the substrate 101 with a working electrode 103a, counter electrode 103b and reference electrode 103c is connected to the conducting tracks 102a, 102b, 102c, where the electrodes are treated with the receptor 105.

Figure 6E:
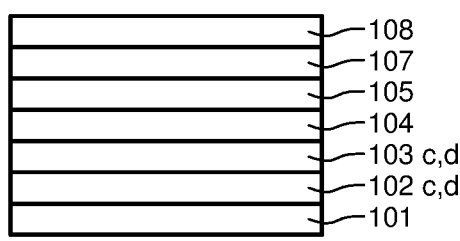
FIG. 6(e) is a cross-sectional view of the electrochemically active and albumin-binding device, where the receptor is arranged on the surface of the membrane and an extra chemical layer of boronic acid derivative is arranged on the surface of second membrane to filter glycated albumin component from the biological sample.

FIG. 6(e), which is a corresponding cross-sectional view depicting a substrate 101 on the surface of which conducting tracks 102d, 102e, 102f are arranged in the right half portion of the substrate 101. A 3-electrode arrangement in the right half portion of the substrate 101 with a working electrode 103d, counter electrode 103e and reference electrode 103f is connected to the conducting tracks 102d, 102e, 102f. The membrane 104 is arranged on surface of the electrodes 103d, 103e and 103f. The receptor layer 105 is arranged on the surface of the membrane 104. Second membrane 107 is arranged on the surface of receptor layer 105. The chemical layer 108 of boronic acid derivatives is arranged on the surface of the second membrane 107 to filter the glycated components from the biological sample.

Figure 6F:
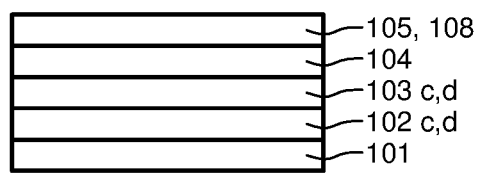
FIG. 6(f) is a cross-sectional view of the electrochemically active and albumin-binding device, where the receptor is arranged on the surface of the membrane and an extra chemical layer of boronic acid derivative is also arranged on the surface of same membrane where the receptor is arranged.

FIG. 6(f), which is a corresponding cross-sectional view depicting a substrate 101 on the surface of which conducting tracks 102d, 102e, 102f are arranged in the right half portion of the substrate 101. A 3-electrode arrangement in the right half portion of the substrate 101 with a working electrode 103d, counter electrode 103e and reference electrode 103f connected to the conducting tracks 102d, 102e, 102f. The receptor 105 and the boronic acid derivatives 108 are arranged on surface of the electrodes 103d, 103e and 103f. The embodiments as shown in FIG. 6 (a) (b), (c),(d),(e) and (f) are used to measure total albumin and albumin without the glycated albumin component in blood samples.

Figure 7:
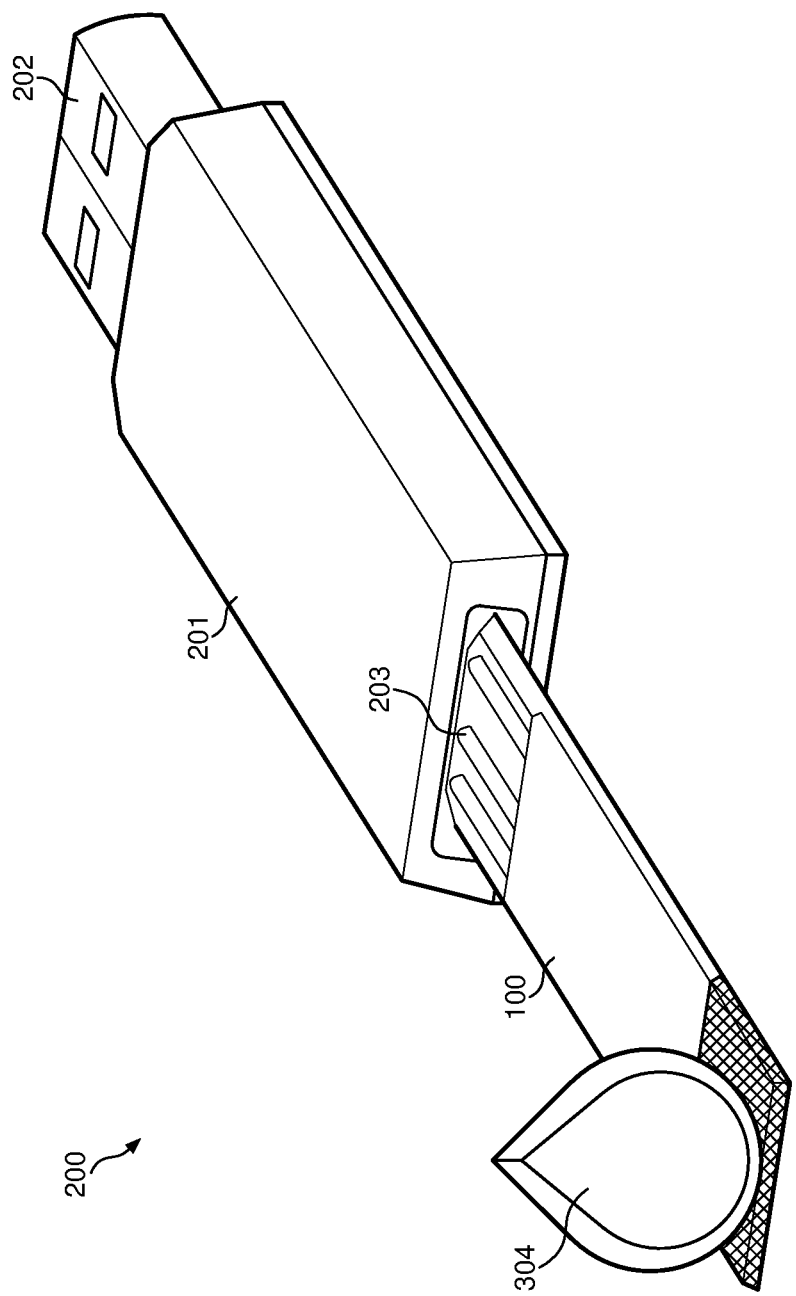
FIG. 7 is a perspective view of device holder holding the device of the present invention.

In yet another aspect of the present invention, a device holder 200 for sensing a bioanalyte in a biological sample is as shown in FIG. 7. The device holder 200 comprises a housing 201 with device detection and conditioning circuit and the housing 201 is adapted to connect to a processor and a display member. A device insertion port 203 is provided in the housing 201. The device 100, which is permitted to pass through the device insertion port 203, includes a substrate with at least a two-electrode member along with an albumin binding and an electrochemically active receptor, connected to the housing 301, and the receptor configured to receive a bio sample 204. A USB plug 202 is connected to the housing 201 as shown in FIG. 7. The device holder 200 is used to collect and retain the biological sample for subsequent testing. The device holder 200 is also provided with device detection, signal conditioning and data acquisition features to identify the type of bioanalyte that is stored on the device 100. The device holder 200 enables the user to insert the holder 200 into a processor and collect the biological sample for measurement.

The device holder 200 of the present invention is powered on after inserting in a processing and display unit. The device 100 is then loaded into the device holder 200. The device detection arrangement of the device holder 200 inside the housing 201 is adapted to indicate to detect the designated device. When the device holder 200 detects the device 100, the device 100 is loaded with the biological sample and a desired redox potential is applied to the working electrode of the device, with respect to the reference electrode, through digital-to-analog converter (DAC). The redox current that is passing through the counter and working electrodes is measured by using a converter voltage to current converter.

Figure 8A:
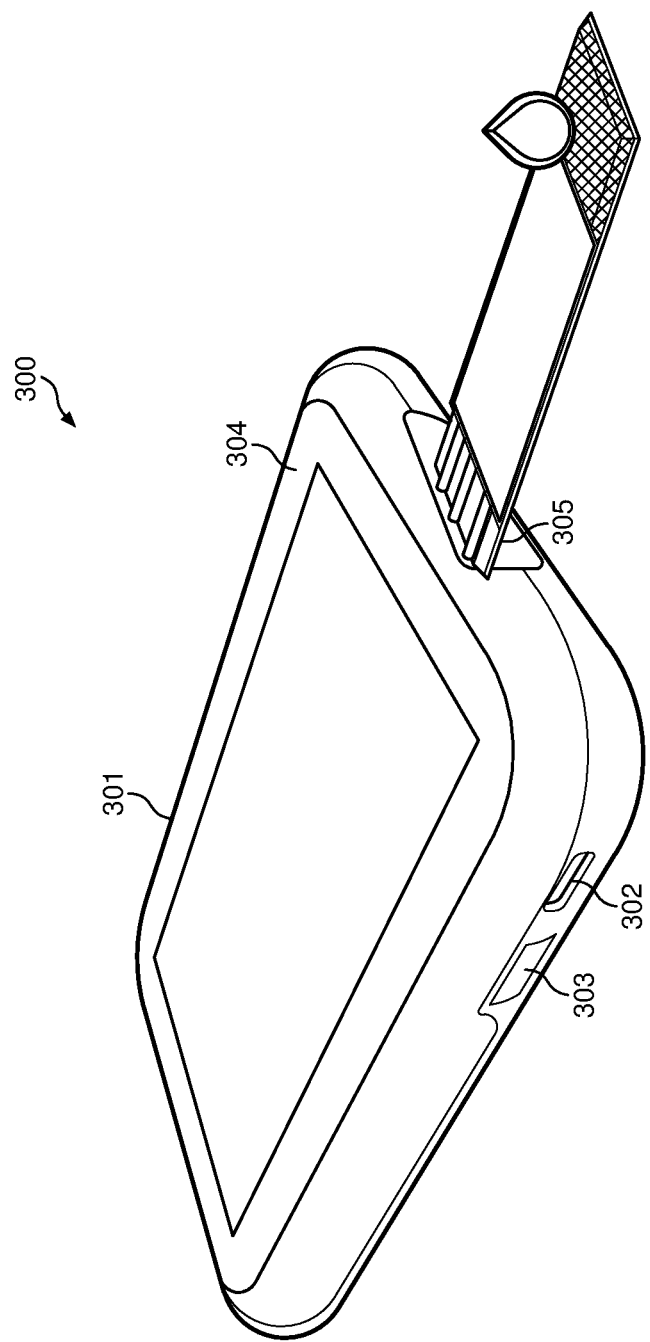
FIG. 8(a) is a perspective view of point-of-care biosensor holding the device of the present invention.

The point-of-care biosensor 300 for sensing a bioanalyte in a biological sample, as shown in FIG. 8(a). The point-of-care biosensor 300 comprises a housing 301, where ports for a micro USB 302 and a micro SD card 303 are provided. The micro USB 302 is used to charge the biosensor 300 and micro SD card is used as a storage device. The housing 301 is also provided with display member 304, which can be an LCD, LED, OLED, OMLED, TFT or any other such display devices, including touch-sensitive devices. A device insertion port 305 is provided in the housing 301. The device insertion port 305 is provided with a metallic contacts to engage the device electrically. In other words, the insertion port 305 is provided to receive the device 100, through the electrode members of the device 100. The point-of-care biosensor 300 is provided to facilitate a user to use the device 100, in a simple way, along with the point-of-care biosensor 300. The device 100 is initially inserted into the point-of-care biosensor 300 and the device 100 is then loaded with a reduced biological sample, in the range of 1-300 μL, which entails a minimum invasive means in collecting the biological sample. The user is also at liberty to use the biosensor 300 at a room temperature not limited by environmental factors such as humidity, temperature variation and storage conditions. The user by using the biosensor 300 is able to measure the concentration levels of the desired bioanalytes, in a substantially shorter period of time, since the bioanalyte binds the receptor, instantaneously. The user is provided with an instantaneous and accurate display of the concentration of the bioanalyte on the display member 304, since the inherent binding nature of bioanalyte is used in the biosensor 300 to measure the concentration levels. By using the biosensor 300 of the present invention, the user is enabled to use the biosensor without a need for active preparation of the biological sample before it is tested.

Figure 8B:
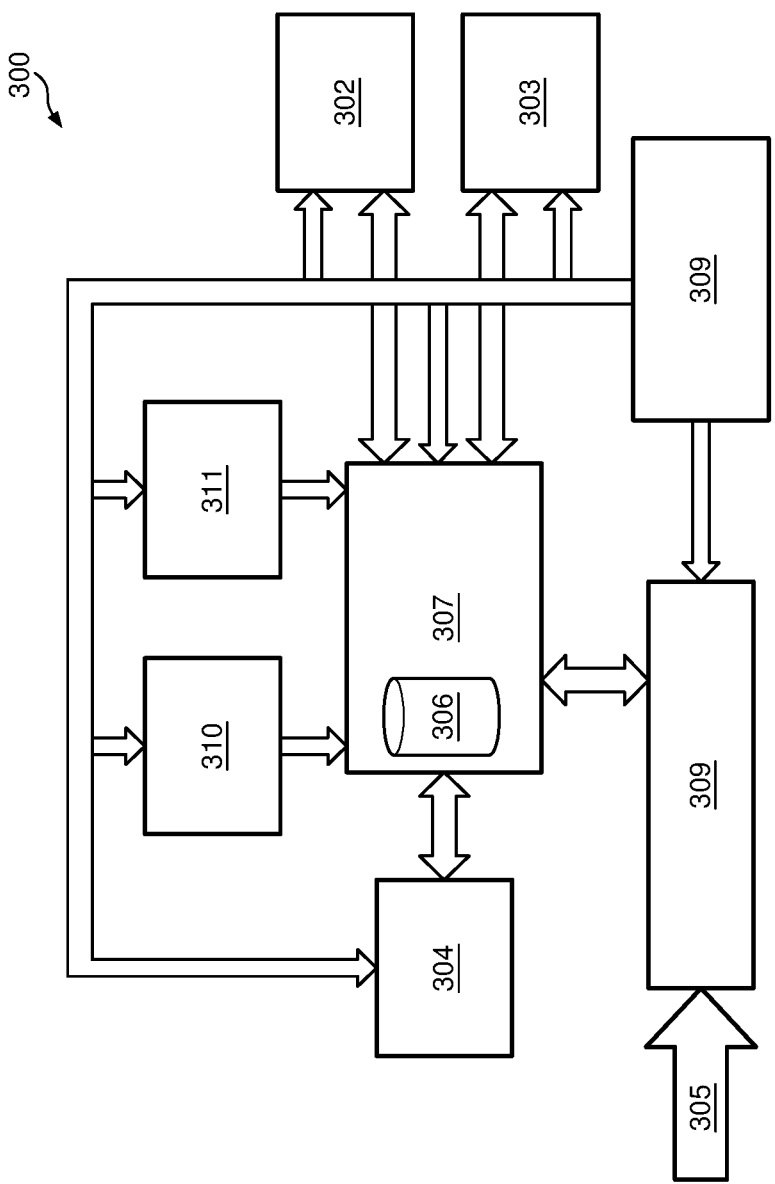
FIG. 8(b) is a schematic depiction of broad internal electronic architecture of the point-of-care biosensor.

Now, referring to FIG. 8(b), an internal electronic hardware architecture of the biosensor 300 is described. A database member 306 is provided in the housing 301 to store standard values of redox current and bioanalyte concentration of human serum albumin (HSA), glycated albumin (GA), methemalbumin (MA) and urine albumin, present in the biological samples. The database 306 also incorporates the data pertaining to historical and current data of concentrations of the bioanalytes. The executables that are required to perform the various functions of the biosensor 300 are stored on a medium of the biosensor 300. A digital controller 307 is provided in the housing 301 and connected to the database member 306 and configured to apply a redox potential to at least a two-electrode member having an electrochemically active and an albumin-binding receptor with a biological sample having an albumin bioanalyte and to measure the corresponding redox current. The digital controller 307 is arranged to measure a redox current of the albumin bioanalyte by linearly matching with the value of concentration and display the value of measured concentration of the albumin bioanalyte.

A power supply to the biosensor 300 is regulated by a power supply unit 308, which is connected to the biosensor 300. The power supply unit 308 includes both online and offline rechargeable battery with charging circuitry. A signal conditioning and device detection unit 309 is connected to the microcontroller 307 to detect the presence of the device 100 in the biosensor 300 and to apply the redox potential to the electrodes and measuring the redox current from the selected biological sample. Humidity and temperature sensors 310 and 311 are arranged in the housing 301. Once the measurement of the concentration levels of the bioanalyte is completed by the microcontroller 307, the concentration levels are displayed on the display member 304, along with historical data of the concentration levels of the bioanalyte.

The present invention also provides a method for an accurate detection and quantitative measurement of albumin bioanalyte in a bio-sample. The desired biological samples such as blood or urine are collected in very small volumes i.e., in the range of micro litres GO, from human subjects, with a minimally invasive means, by following standard protocols. In the method of present invention the preferred volume of the biological sample that can be used for the measurement of bioanalyte is preferably in the range of 1-300 micro litres (μL). The required volume of the biological sample is subject to the size of the surface area of the receptor of the device. The reduced collection of sample substantially reduces trauma in the subjects, since it is obtained through a minimally invasive sample extraction technique. The reduced volume of biological samples avoids the need for a user to phlebotomy collection products.

In the method of the present invention, the determination and accurate measurement of a bioanalyte, is performed by implementing the principle of electrochemistry. Accordingly, the bioanalyte that is advantageously selected for its measurement is a globular protein—human serum albumin (HSA), and urine albumin through a measurement of redox current flowing through electrochemically-active devices, on the application of an electric potential. The method of the present invention also measures the quantities of albumin complexes such as glycated albumin (GA) and methemalbumin (MHA). In the present invention particularly the quantitative measurement of GA, which is a known electrically insulated biomolecule without having any metallic prosthetic group, is performed.

In the present invention the receptor substance is selected from a group consisting of metal porphyrin ligands, metal ions, organic molecules and combination of the se substances.

In the method of present invention the receptor substance is prepared, advantageously as a solution of preferred chemical substances as hereinafter described. For instance, in case hemin is selected as a preferred receptor, hemin is dissolved preferably in an alkaline aqueous solution (NaOH/KOH) or dimethyl sulphoxide (DMSO), or any other solvents which can dissolve these substances.

In case of a receptor substance, which is based on Cu(II) chemical substances, preferably $CuCl_2$ and $Cu_2SO_4$, the chemical substance is preferably dissolved in distilled water, alcohol, ammonium hydroxide or any other solvents, which can dissolve these substances.

In the event methylene blue (MB) is used as a receptor, the chemical substance is preferably dissolved in distilled water or any other solvents, which can dissolve this chemical substance.

The receptor solution thus prepared is applied to the electrode members or electrode members with membranes of the device of the present invention, prior to the application of biological samples.

Alternately, the receptor solution can also be premixed with the biological samples and the mixed solution is applied to the electrode members or electrode members with membranes of the device.

Figure 9:
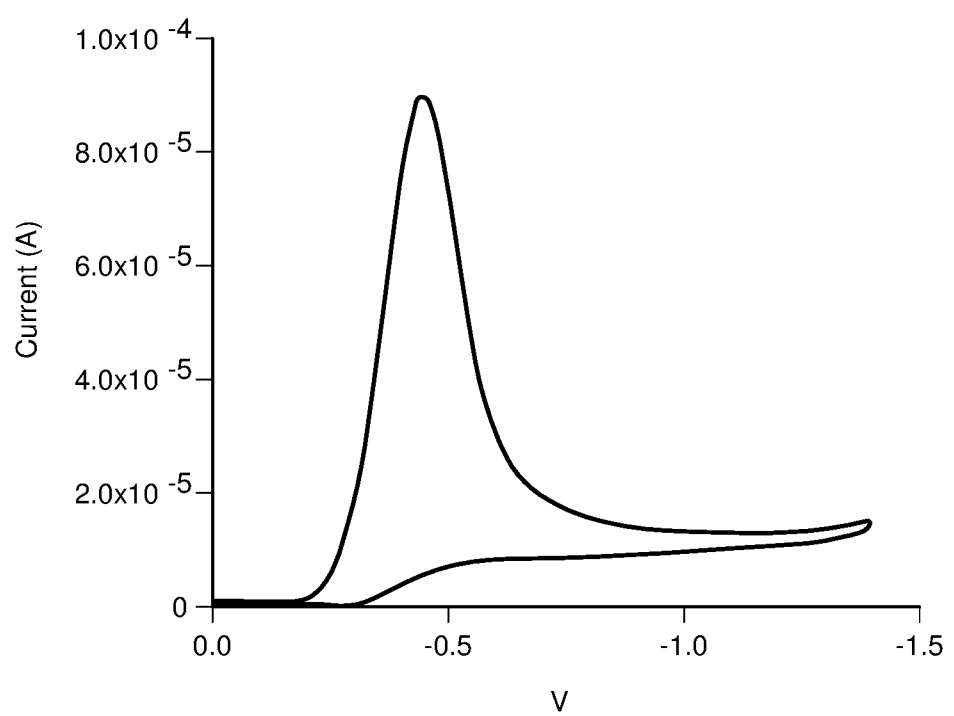
FIG. 9 is a plot depicting reduction peak of hemin in urine biological sample.

In an exemplary aspect the method for detection and measurement of urine albumin is now described. In order to test the presence of albumin in a urine sample, the reduced volume of the biological sample (urine) is brought in chemical contact with the receptor of the device of the present invention. The receptor is a metal porphyrin substance, which is hemin. Human albumin is known to bind different substances such as fatty acids, metal ions, hemin, bilirubin and pharmaceutical drugs such as warfarin, acetylsalicylic acid. Albumin binds hemin with a high association constant. The association constant for hemin is $1.1\times10^8$ $M^{-1}$ and hemin is electrochemically active, as shown in FIG. 9. Hemin contains iron in ferric form (Fe(III)) and this reduces into ferrous (Fe(II)) form under cyclic voltammetry as shown in the equation $Fe(III)+e^-\rightarrow Fe(II)$, where a reduction peak, as shown in FIG. 9, is obtained. In view of binding of albumin to hemin and hemin exhibiting a reduction current peak, hemin is selected as a ligand receptor, to detect albumin concentration. The peak reduction current of free hemin as shown in FIG. 9, is used to compare the variance in the corresponding peak reduction current, when hemin binds albumin in the urine samples.

Prior to the measurement of albumin concentration in desired biological sample. Data pertaining to standard albumin concentrations (mg/L) in various urine synthetic urine samples are collected and stored in a database member. Thus the database member is populated with the values of standard urine albumin concentrations (mg/L) along with the corresponding redox current values (μA) of hemin. The preferred redox current values for the designated concentrations are obtained in an iterative manner, where repeated tests, result in identical redox current values, for the selected albumin concentration.

Figure 10:
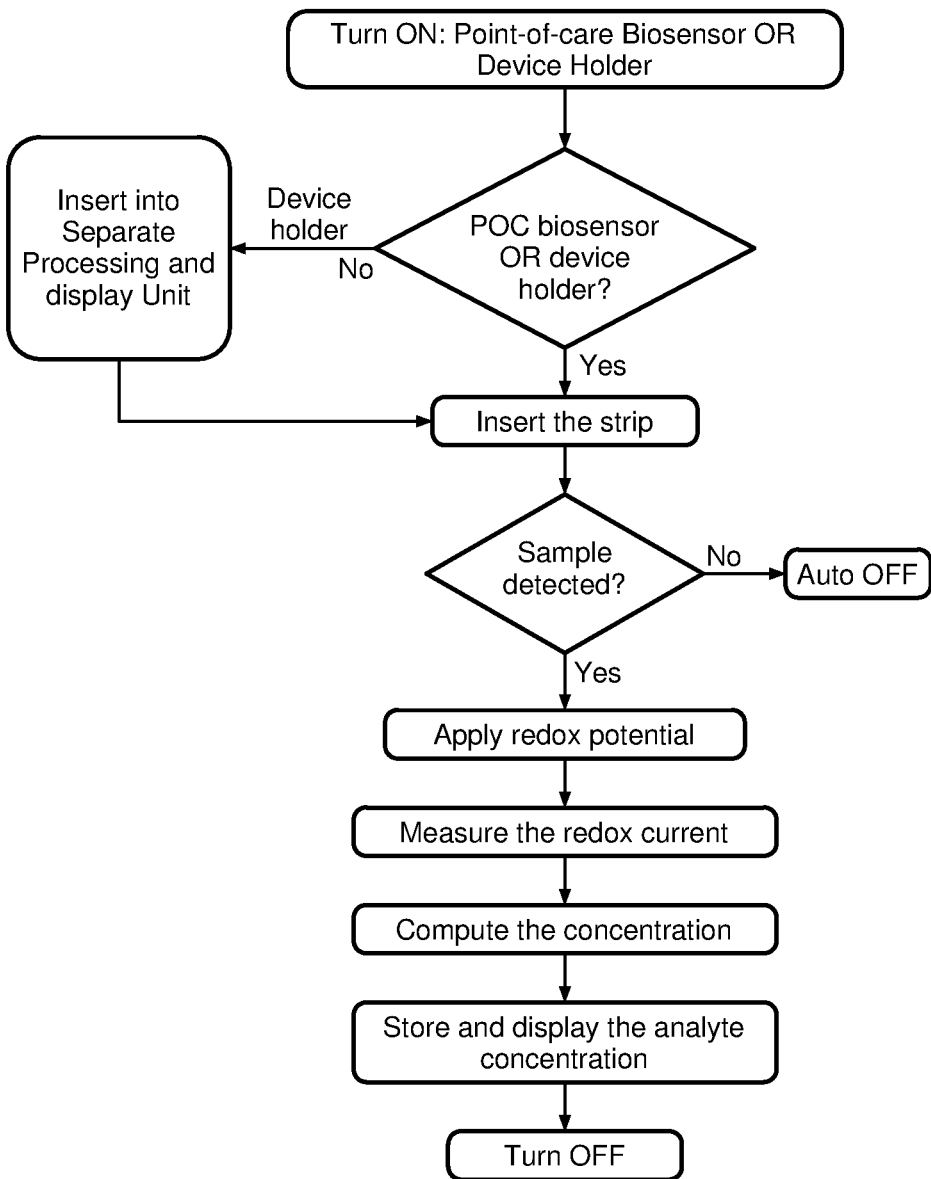
FIG. 10 is a high-level flow chart depicting process steps to measure quantitatively the concentration of the bioanalytes by using the device and point-of-care biosensor of the present invention.

Now, process steps of the measure of bioanalyte are described by referring FIG. 10(a) and FIG. 10(b). The biosensor of the present invention is selected and powered on. The device is then loaded into the biosensor. The biosensor is adapted to indicate to detect the designated device. When the device is detected by the biosensor the device is loaded with the biological sample and a desired redox potential is applied by digital-to-analog converter (DAC) to the working electrode of the device with respect to the reference electrode. Redox potential is a measure of the tendency of a chemical substance to acquire electrons and thereby be reduced. Each chemical substance has its own intrinsic redox potential. The more positive the potential, the greater is the substance affinity for electrons and the tendency to be reduced. Accordingly, the redox potential of hemin in artificial urine solution can be in about −0.5 V. The redox current that is passing through the counter and working electrodes is measured by using V to I converter.

The measured redox current is matched with the stored redox current values and the matching urine albumin concentration is secured and displayed by the biosensor. Alternately, the linear-fit equation can also be used to compute the concentration of bioanalyte by using the redox current value. The biosensor after having extracted the value of concentration of albumin in the urine sample displays the value.

In another aspect of the present invention human blood plasma is used as a biological sample to determine albumin content. The aforementioned receptors are used with this biological sample along with the steps as described above, to determine the albumin content.

Figure 11:
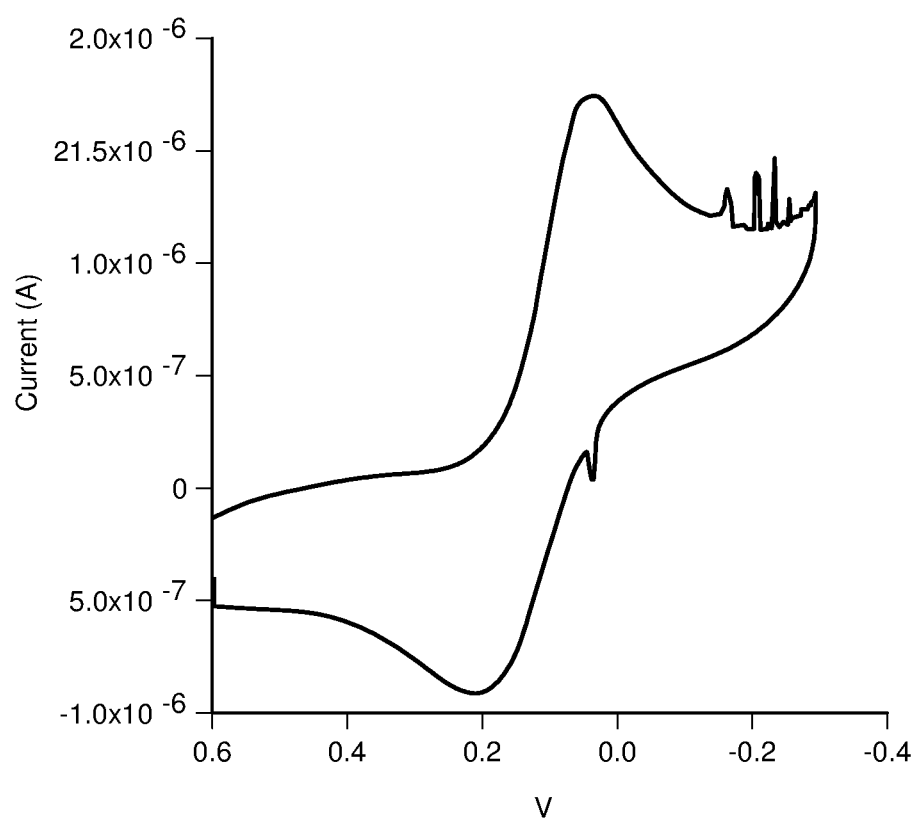
FIG. 11 is a plot depicting redox behaviour of $CuCl_2$ is a synthetic urine solution.

In an exemplary aspect, $CuCl_2$ is adopted as a receptor to bind plasma albumin. Albumin binds Cu(II) with a highest association constant. The association constant for Cu(II) is $1.6\times10^{16}M^{-1}$ and Cu(II) is electrochemically active, as shown in FIG. 11. $CuCl_2$ contains copper with oxidation state +2 and reduced into Cu(0) in where a reduction peak obtained along with an oxidation peaks, as shown in FIG. 11 is obtained. In view of binding of Cu with albumin, a decrease in reduction and oxidation peaks is observed, which is linearly proportional to the variation in the concentration of the albumin in the biological sample. In view of binding of albumin to Cu(II) and Cu(II) exhibiting a reduction and oxidation current peak, Cu(II) is selected as a receptor, to detect albumin concentration.

Figure 12:
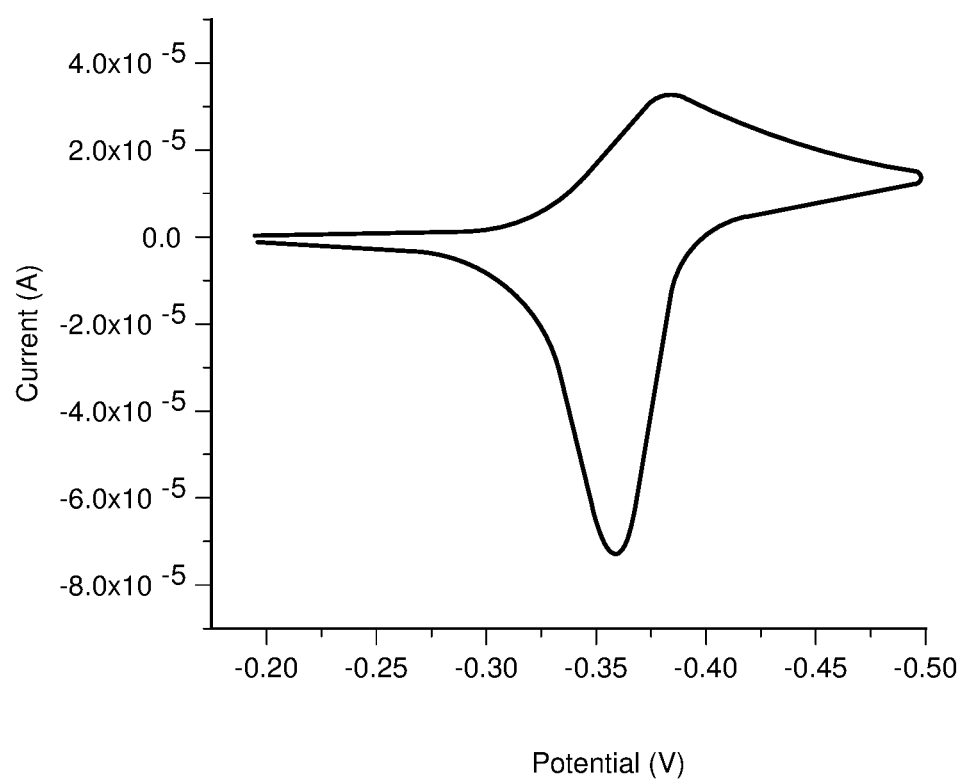
FIG. 12 is a plot depicting cyclic voltammogram of methylene blue (MB).
Figure 13:
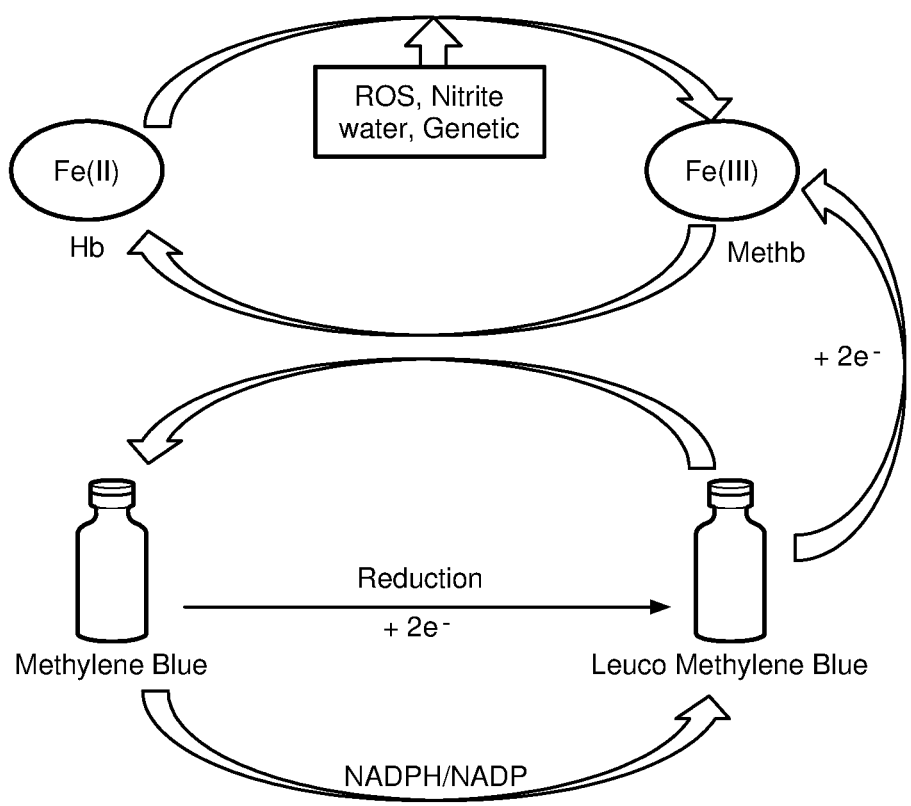
FIG. 13 is a schematic expression of redox behavior of methylene blue in methaemoglobinaemia.

Methylene blue (MB) is a well-known electrochemical redox-dye. MB demonstrates a reversible redox peaks in cyclic voltammogram as shown in FIG. 12. MB is commonly used in biology for DNA staining and as an antidote for methaemoglobinaemia disorder. In methaemoglobinaemia treatment, MB reduces (by gaining electrons) into leucomethylene blue (LMB), in the presence of nicotinamide adenine dinucleotide phosphate (NADPH) enzyme. Thereafter, LMB donates its electron to the ferric form ($Fe^{+3}$) of iron in methemoglobin molecule and converts it back into ferrous form ($Fe^{+2}$) in hemoglobin molecule. The reduction of MB into LMB in the presence of NADPH enzyme is the key to this process as shown in FIG. 13. In the present invention, MB is reduced into LMB by electrochemical route using cyclic voltammetry technique. If any $Fe^{+3}$ containing element or an elemental ferric iron is added in the reduced form of the MB (LMB), then MB donates its electron to ferric form ($Fe^{+3}$) and reduces it into ferrous form of iron ($Fe^{+2}$). In this reaction, LMB further oxidized into MB form while Iron in $Fe^{+3}$ form reduced into Iron $Fe^{+2}$ form, as shown in the following reaction:

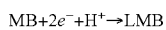

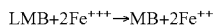

Figure 14:
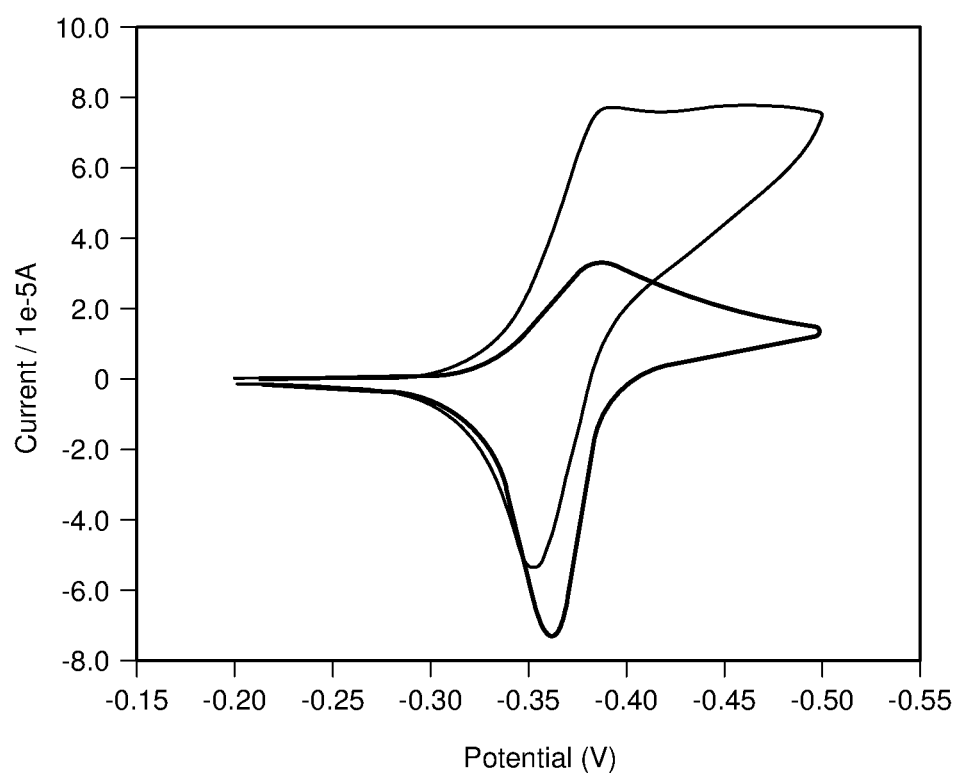
FIG. 14 depicts plots of cyclic voltammograms of methylene blue (MB) with and without an addition of hemin.
Figure 15:
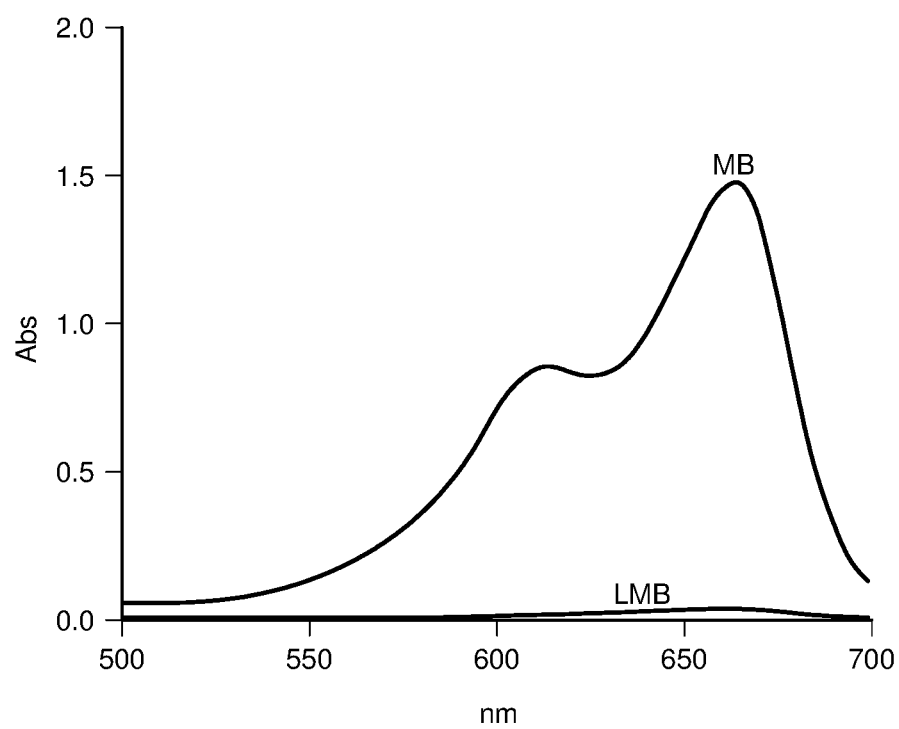
FIG. 15 is a plot depicting UV-VIS spectra of MB and leucomethylene blue (LMB).
Figure 16:
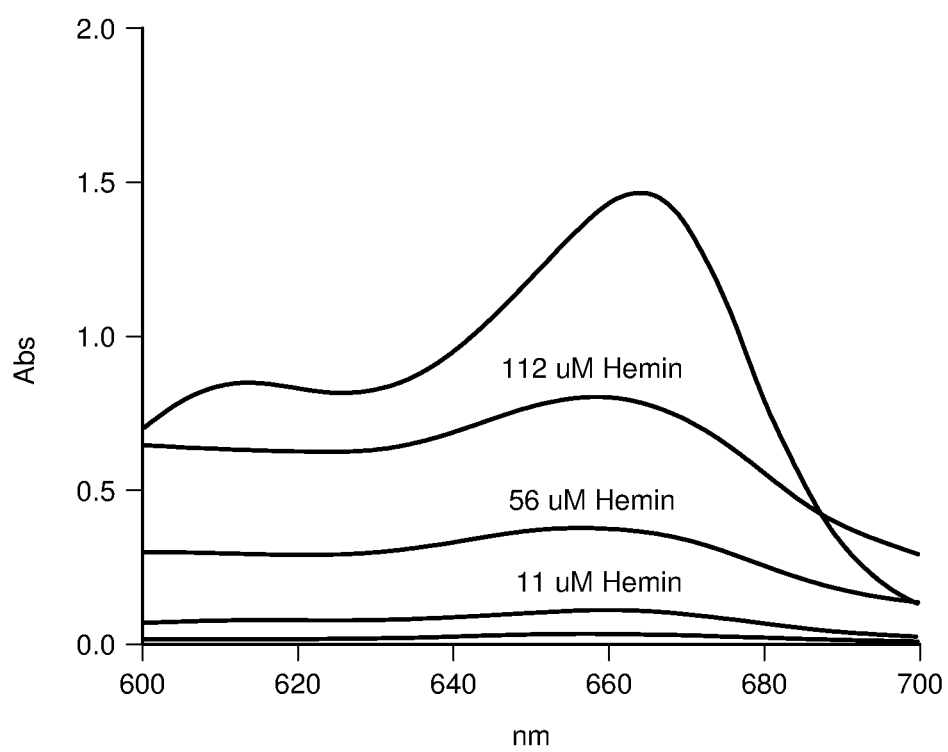
FIG. 16 depicts UV-VIS spectra of leucomethylene blue with different concentrations of hemin.
Figure 17:
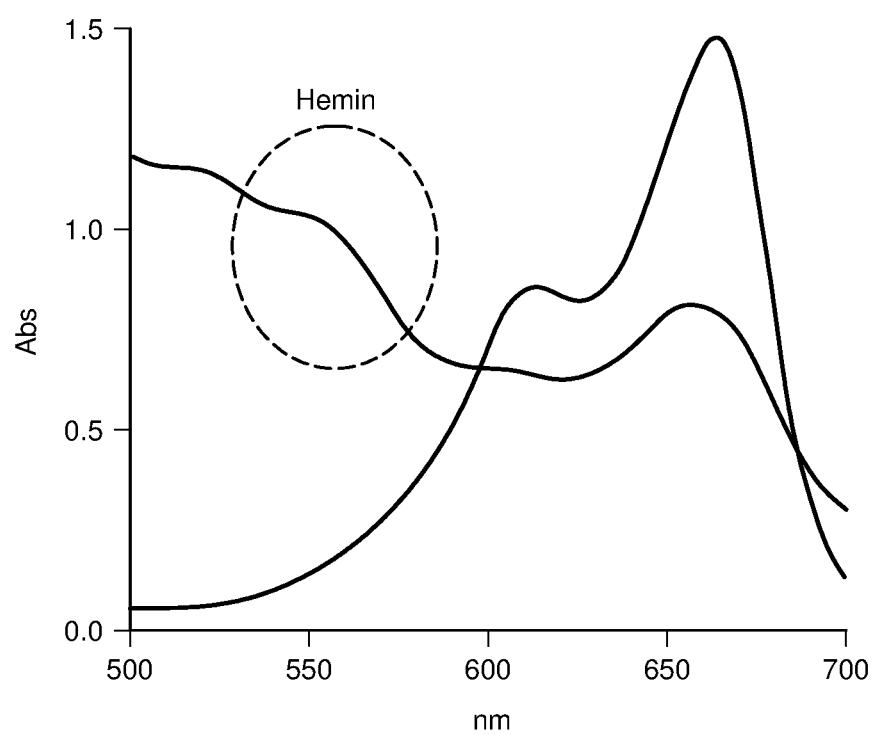
FIG. 17 depicts UV-VIS spectra of methylene blue and hemin converted methylene blue.
Figure 18:
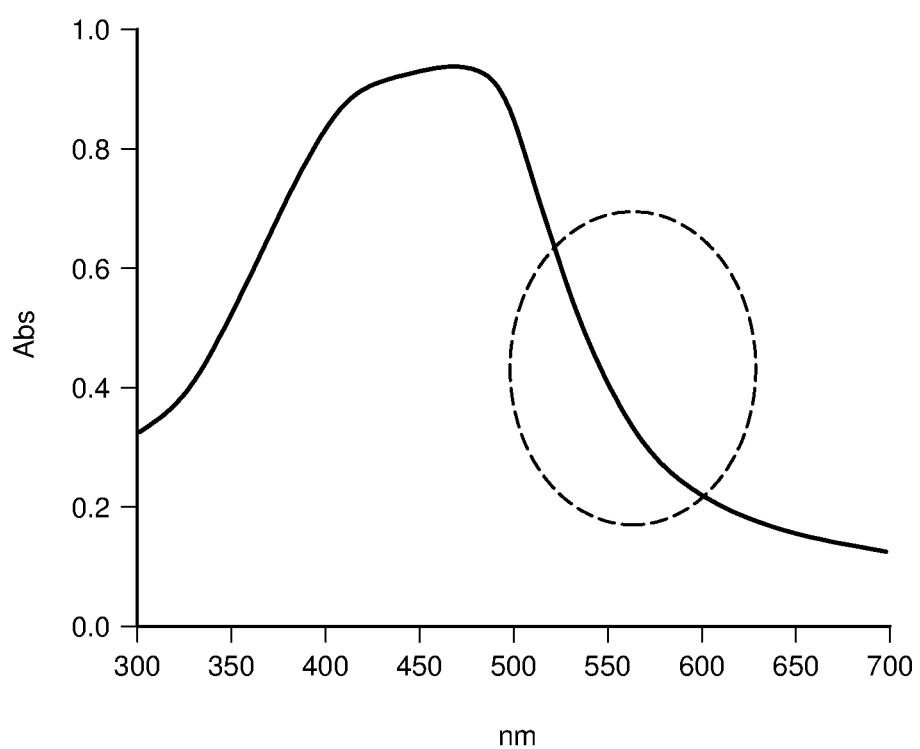
FIG. 18 depicts UV-VIS spectrum of hemin.

The reduction current peak of MB increases after adding the hemin because of catalytic current flow due to the donation of electrons from LMB to $Fe^{+3}$, as shown in FIG. 14. This reaction is analyzed using ultraviolet visible (UV- VIS) spectroscopy. MB demonstrates an absorption peak at about 660 nm, while LMB is a colorless liquid and it does not show any absorption peak in UV-VIS spectrum as shown in FIG. 15. Here, LMB solution is prepared by chemical reduction of MB using ascorbic acid. After adding the hemin in LMB solution, LMB oxidizes into MB by donating its electrons to hemin and MB peaks appears as shown in FIG. 16. If comparison of UV-VIS spectra of pure MB is made with the hemin converted MB, then an increase in absorption is observed below 600 nm as shown in FIG. 17. This increase in absorption is due to the presence of hemin in the MB sample as shown in FIG. 18.

Based on aforementioned principle of activity of hemin with MB, in the method of present invention, a combination of hemin-MB based receptor is adopted for albumin detection.

Figure 19:
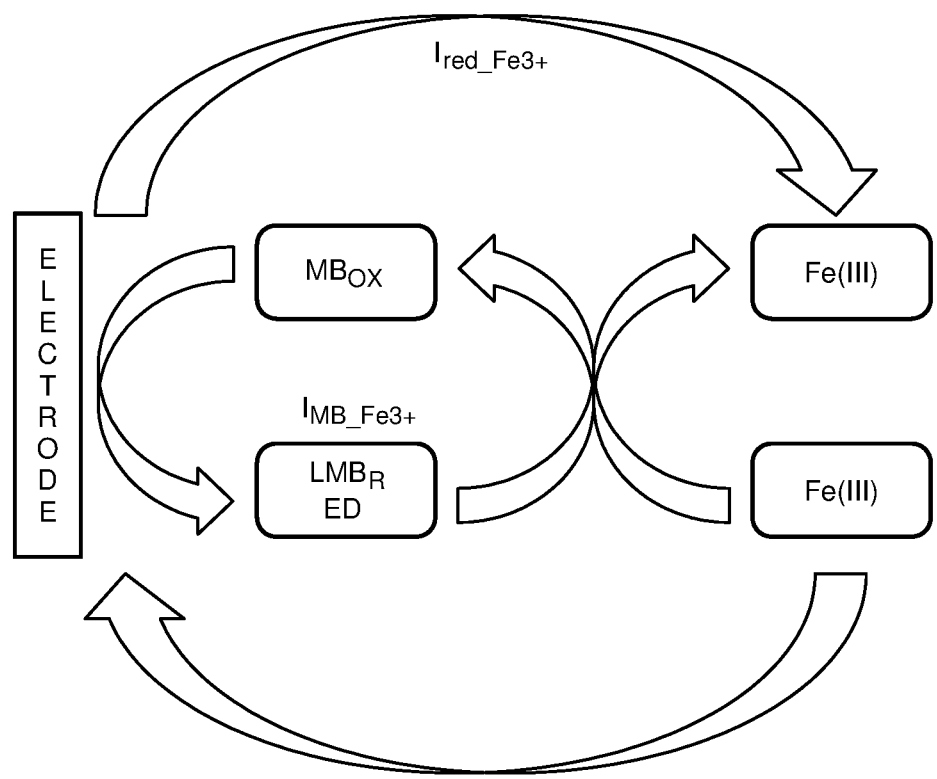
FIG. 19 is a schematic reaction mechanism of MB-hemin based detection.

In hemin-MB based albumin detection, the higher peak reduction current thus measured even at lower hemin concentration is attributed to reduction of hemin by LMB by donating electrons and some hemin molecules directly reduce at the electrode surface, same as in the case of direct detection, as shown in FIG. 19. Accordingly, a small amount of MB acts as a current amplifier.

In the hemin based direct detection of urine albumin, the hemin is reduced at the electrode surface and a corresponding reduction current is obtained. Whereas, in in the case of MB-hemin based detection, hemin is also reducing by the donation of electrons from LMB molecule to the hemin molecule similar peak current in MB-hemin based detection is obtained even at lower hemin concentration. In this way, the usage of hemin is substantially reduced so by using the combination of MB-hemin while getting the same reduction current values.

The measured redox current is matched with the stored redox current values and the matching urine albumin concentration is secured and displayed by the biosensor. Alternately, the linear-fit equation can also be used to compute the concentration of bioanalyte by using the redox current value. The biosensor after having extracted the value of concentration of albumin in the urine sample displays the value.

Figure 20A:
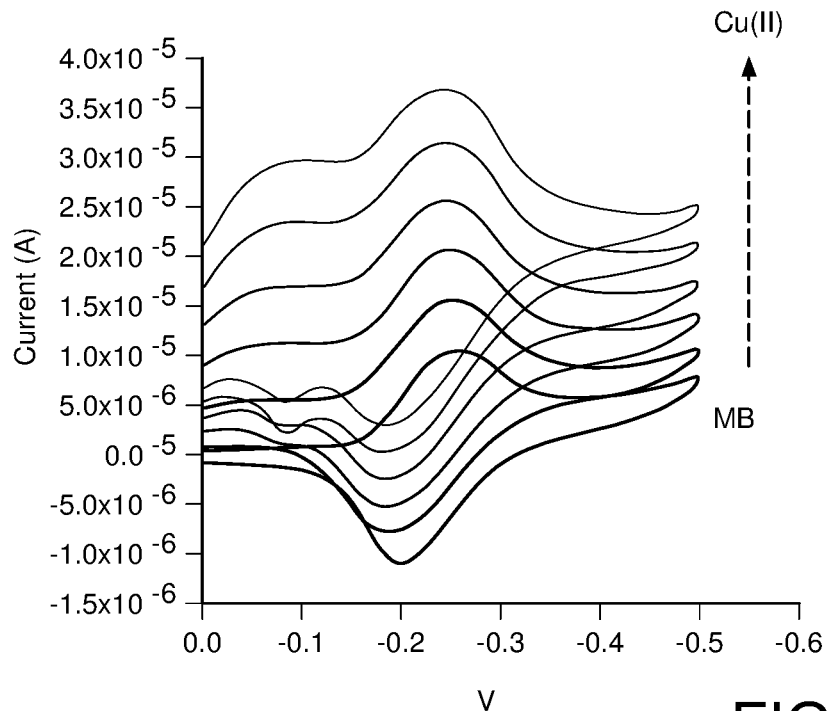
FIG. 20(a) depicts cyclic voltammogram of MB prior to the addition of $CuCl_2$.
Figure 20B:
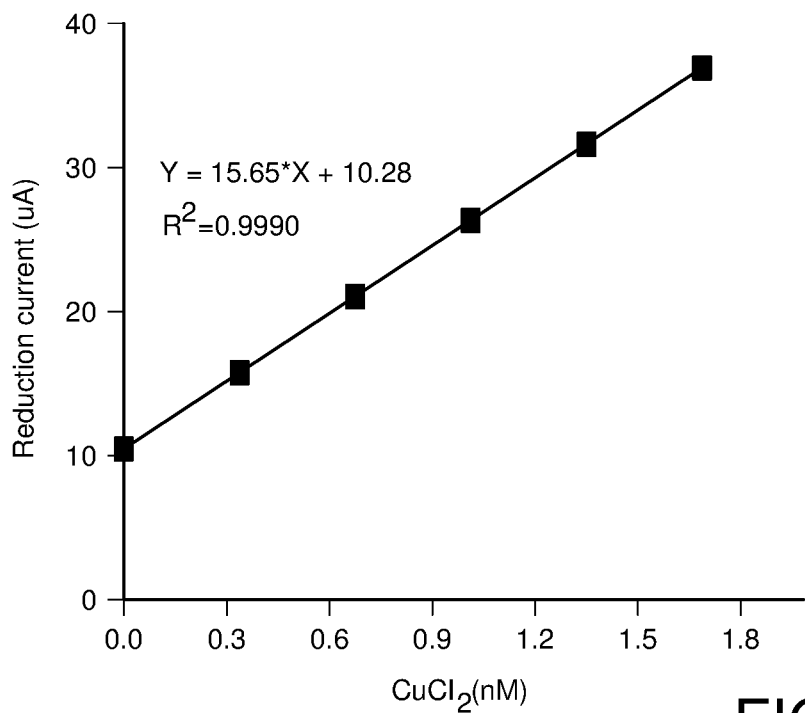
FIG. 20(b) depicts a plot of reduction current versus $CuCl_2$ concentration.

In another aspect of present invention, a combination of MB-$CuCl_2$ receptor is used. When this type of receptor is used there is an increase in the peak reduction current in MB cyclic voltammogram after adding the Cu (II), because of catalytic current, as discussed earlier in the case of MB-hemin reaction, as shown in FIG. 20. Copper-Albumin complex is known to have the super oxide dismutase activity and can quench the electrons from the reduced form of MB. In case, the combination of $CuCl_2$-MB as a receptor for urine albumin detection then the peak reduction current increases because of the fact that when we add the albumin in the Cu (II)-MB solution then the copper-albumin complex increase the oxidation of methylene blue by quenching the electron from the reduced form of MB (LMB) and increase the concentration of MB at the electrode surface.

The measured redox current is matched with the stored redox current values and the matching urine albumin concentration is secured and displayed by the biosensor. Alternately, the linear-fit equation can also be used to compute the concentration of bioanalyte by using the redox current value. The biosensor after having extracted the value of concentration of albumin in the urine sample displays the value.

In another aspect of the present invention human blood plasma is used as a biological sample to determine albumin content. The aforementioned receptors are used with this biological sample along with the steps as described above, to determine the albumin content.

In another aspect of the method of the present invention, $CuC_{l2}$ is adopted as a receptor to bind plasma albumin. Albumin binds Cu(II) with a highest association constant. The association constant for Cu(II) is $1.6 \times 10^{16}$ $M^{-1}$ and Cu(II) is electrochemically active, as shown in FIG. 11. $CuC_{l2}$ contains copper with oxidation state +2 and reduced into Cu(0) in where a reduction peak obtained along with an oxidation peaks, as shown in FIG. 11 is obtained. In view of binding of Cu with albumin, a decrease in reduction and oxidation peaks is observed, which is linearly proportional to the variation in the concentration of the albumin in the biological sample. In view of binding of albumin to Cu(II) and Cu(II) exhibiting a reduction and oxidation current peak, Cu(II) is selected as a receptor, to detect albumin concentration.

It is to be noted here a description for the measurement of albumin bioanalyte in the blood sample, by using $CuCl_2$ as a receptor. The other suitable receptors such as hemin, MB-hemin, MB-$CuCl_2$ can also be used to determine the concentration of albumin.

In a further aspect of the present invention, the concentration of glycated albumin is determined by using the biosensor of the present invention. The biosensor thus used is advantageously provided with an electrode configuration as shown FIG. 6 (a). Each of two sets of electrodes is treated with $CuCl_2$ and one of the sets of electrodes is provided with a membrane treated with boronic acids or their derivatives.

Boronic acids and boronic acids derivatives have an affinity towards carbohydrates such as glucose, glycated proteins such as glycated haemoglobin, glycated albumin. In the present invention boronic acids affinity principle (or Boronate affinity principle) is used to separate the glycated albumin component from the total albumin component.

Figure 21:
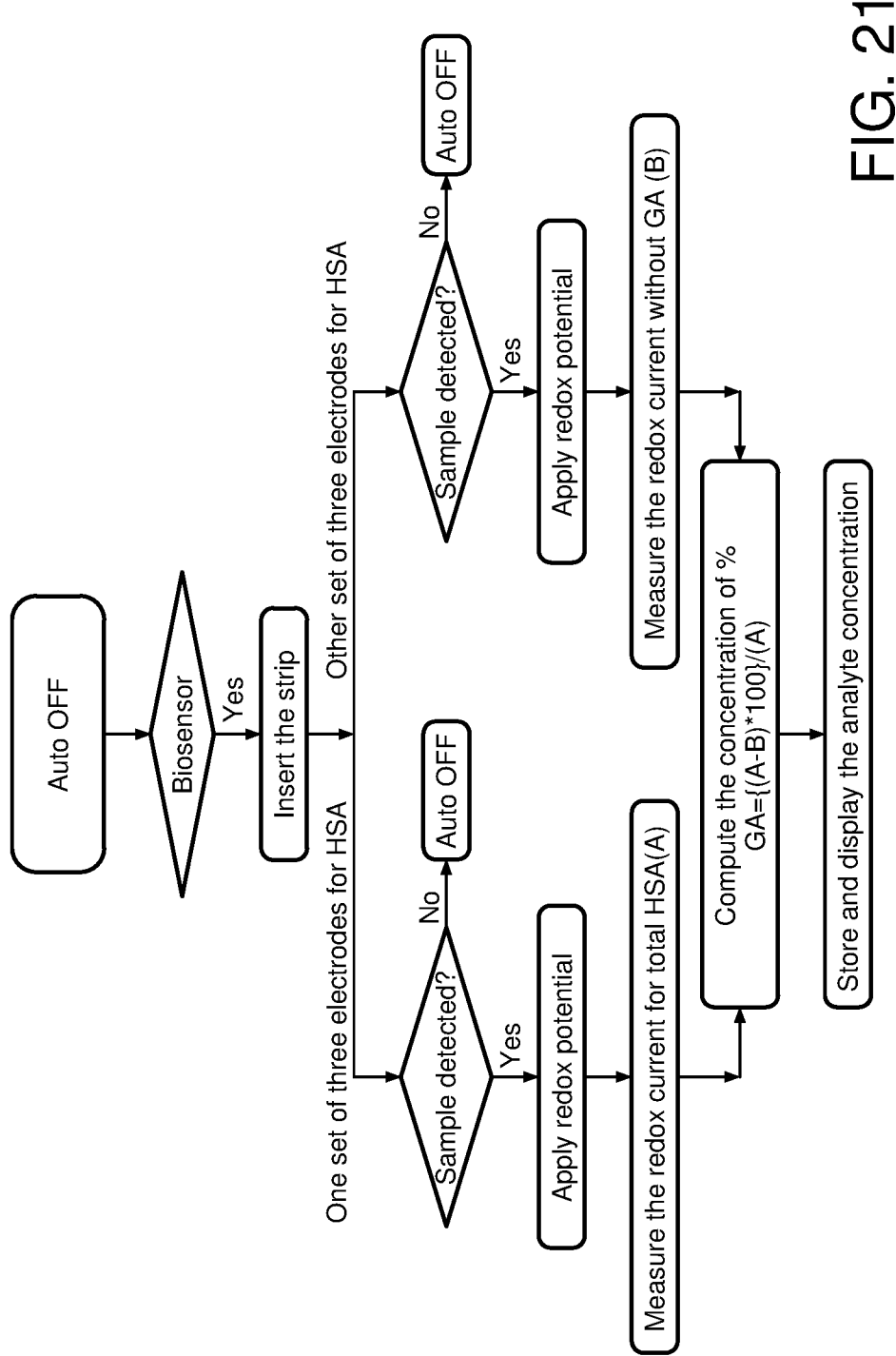
FIG. 21 is a high-level flow chart depicting is a high-level flow chart depicting process steps to measure quantitatively the concentration of the glycated albumin by using the device and point-of-care biosensor of the present invention.

A reduced quantity of blood or blood plasma is applied on both the sets of electrodes and process steps as shown in FIG. 21. Redox potential is applied to both the sets of the electrodes and the corresponding redox current is measured from these electrodes. By computing the difference in measured redox current in both the electrodes, the concentration of the glycated albumin is obtained.

In another aspect of the present invention steps to determine the methemalbumin concentration in human blood plasma are described. Methemalbumin is a complex of hemin and albumin, in which iron is present in ($Fe^{+3}$) form. Methemalbumin complex is prepared by using HSA and bovine hemin in the manner as described in the literature. The receptor that is used is MB.

The measured redox current is matched with the stored redox current values and the matching urine albumin concentration is secured and displayed by the biosensor. Alternately, the linear-fit equation can also be used to compute the concentration of bioanalyte by using the redox current value. The biosensor after having extracted the value of concentration of albumin in the urine sample displays the value.

The subject matter of the invention is now illustrated in the form of the following examples. These examples are provided for purpose of illustration and shall not be construed as limiting the scope of the invention.

Example 1: Determination of Urine Albumin Concentration and Corresponding Reduction Current Using Hemin as a Receptor Synthetic urine is prepared by dissolving 14.1 g of NaCl, 2.8 g KCl, 17.3 g of urea, 19 ml ammonia water (25%), 0.60 g $CaCl_2$ and 0.43 g $MgSO_4$ in 0.02 mole/L of HCl. The final pH of synthetic urine is adjusted to 6.04 with using HCl and ammonia water. 1-6 mg of hemin is dissolved in 20 ml solution of 0.1 to 1 N NaOH in distilled water. The solution is further diluted with distilled water. The final volume of hemin solution is 40 ml and pH is 11.5. The 20 µL volume of hemin solution is used as a receptor for urine albumin detection. 3 mg of human albumin is dissolved in 10 ml of synthetic urine solution to prepare the micro albumin solution. From this master solution, different concentrations of microalbumin solutions are prepared by appropriate dilution. A constant volume of receptor (such as 20 µL) is premixed with varying concentration of micro albumin solution to get a final volume 300 µL for testing.

Figure 22A:
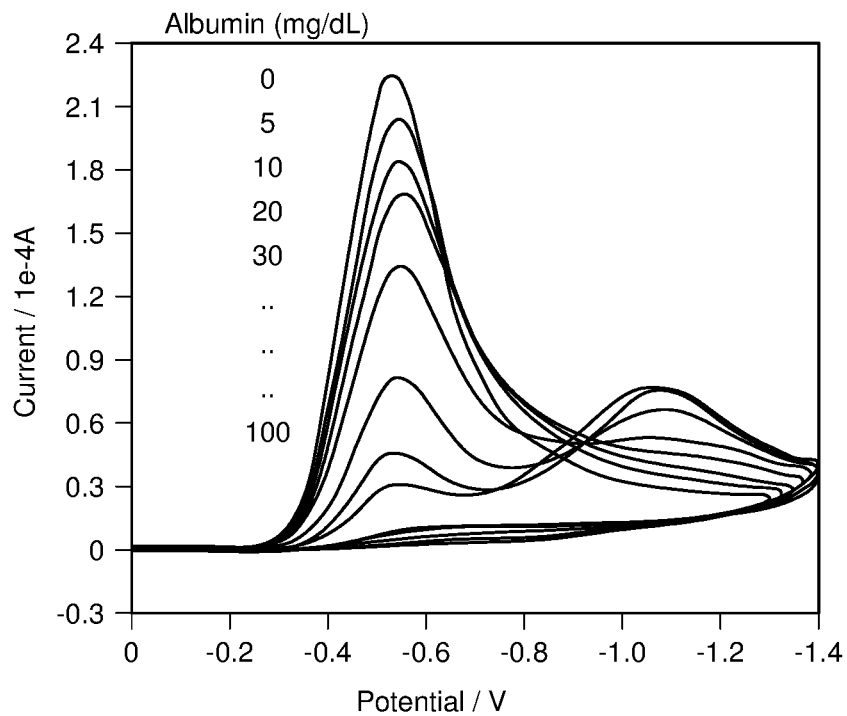
FIG. 22(a) depicts cyclic voltammogram of free hemin with different urine albumin concentrations

A desired volume of the biological sample (urine) is taken and dispensed on the electrode of the biosensor device and the corresponding cyclic voltammogram is obtained by values using the CHI-Electrochemical workstation using the potential window varies from 0 V to −1.4 V with scan rate of 0.1 V/sec., as shown in FIG. 22(a).

Figure 22B:
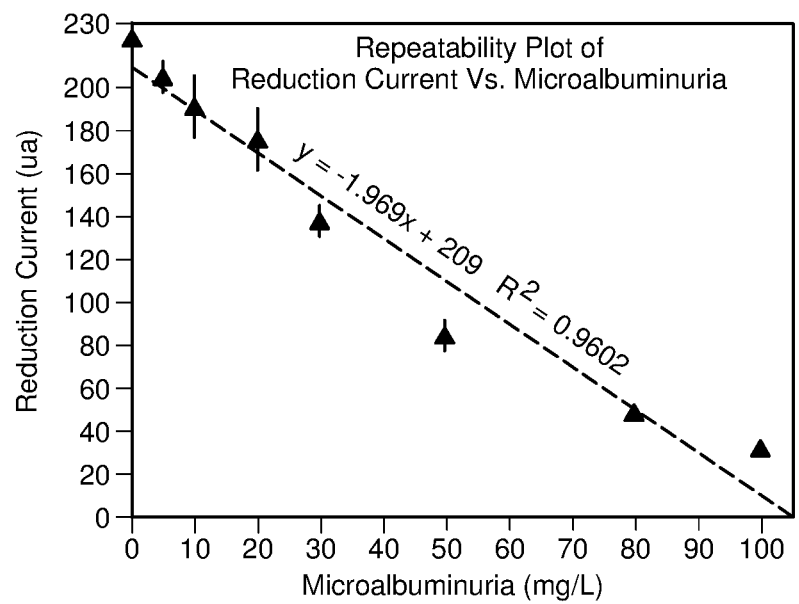
FIG. 22(b) depicts reduction current plot versus urine albumin concentration

The albumin content in the urine sample binds hemin thereby demonstrating a linear decrease in peak reduction current with urine albumin concentration as shown in FIG. 22(a) and FIG. 22(b). If the concentration of albumin in urine sample is increased then the albumin increasingly binds with hemin thereby reducing the free hemin concentration on the electrode resulting in the decrease in peak reduction current of free hemin.

The values of concentrations of the urine albumin (mg/L) along with corresponding reduction current values (µA) are recorded and tabulated as shown in Table 1. Table 1 can be prepared from linear fit equation as given below:

$$y=-1.96x+209$$

In the above equation "y" represents the redox current value and "x" represents the concentration of analyte.

TABLE 1

| Urine Albumin Concentration (mg/L) | Reduction current (µA) |
| --- | --- |
| 0 | 222 |
| 5 | 203 |
| 10 | 182 |
| 20 | 167 |
| 30 | 133 |
| 50 | 81 |
| 80 | 46 |
| 100 | 30 |

Example 2: Measurement of Urine Albumin with Hemin Receptor

A sample volume of synthetic urine of 300 uL is placed on the electrode having the hemin receptor of 1-5 µg then the peak reduction current value is noted from cyclic voltammogram specifying a potential window from 0V to −1.4V in CHI Electrochemical workstation. The value of peak reduction current is 200 µA. This current value is searched in the Table 1 and the corresponding concentration of urine albumin is obtained is 5 mg/L.

Example 3: Determination of Values of Urine Albumin Concentration and Corresponding Reduction Current Using Copper as a Receptor Synthetic urine is prepared by dissolving 14.1 g of NaCl, 2.8 g KCl, 17.3 g of urea, 19 ml ammonia water (25%), 0.60 g $CaCl_2$ and 0.43 g $MgSO_4$ in 0.02 mole/L of HCl. The final pH of synthetic urine is adjusted to 6.04 with using HCl and ammonia water. 5 to 25 mg of $CuCl_2$ is dissolved in 50 ml solution artificial urine. The 204 volume of this solution is used as a receptor for urine albumin detection. 2 mg of human albumin is dissolved in 10 ml of synthetic urine solution to prepare the micro albumin solution. 204 micro drop of receptor is premixed with the micro albumin solution with known concentrations and make the final volume 220 µL.

Figure 23A:
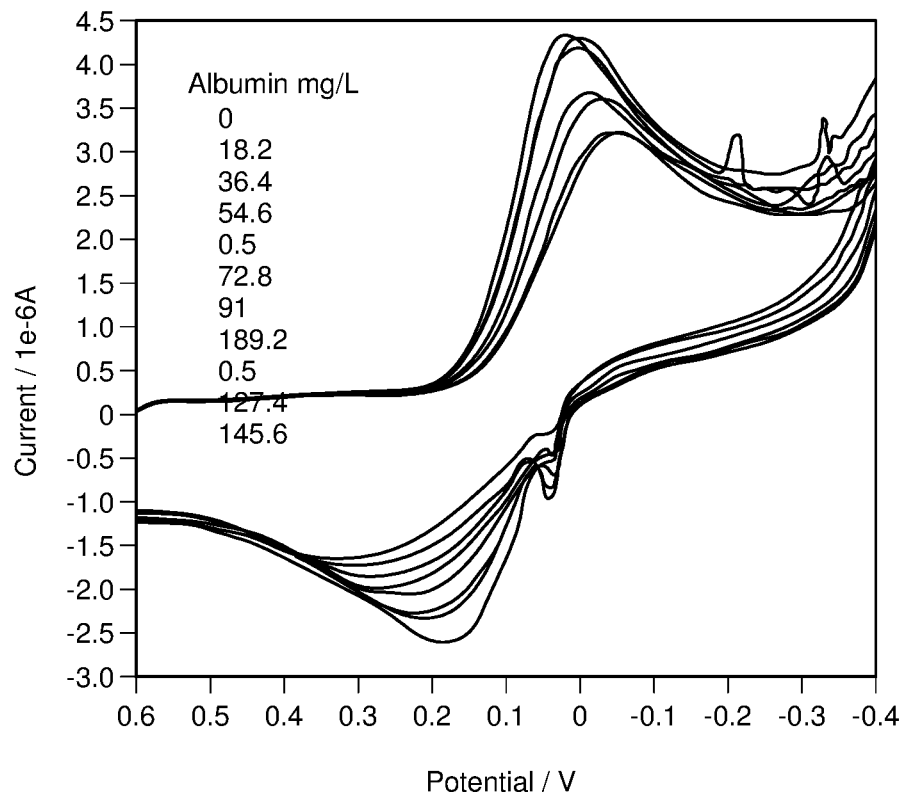
FIG. 23(a) is a cyclic voltammogram of free Cu(II) in $CuCl_2$ with different urine albumin concentrations

A desired volume of the biological sample (urine) is taken and dispensed on the electrode of the biosensor device and the corresponding cyclic voltammogram is obtained by using the CHI Electrochemical workstation with the potential window varies from 0.6 V to −0.4 V with scan rate of 0.15 V/sec as shown in FIG. 23 (a).

Figure 23B:
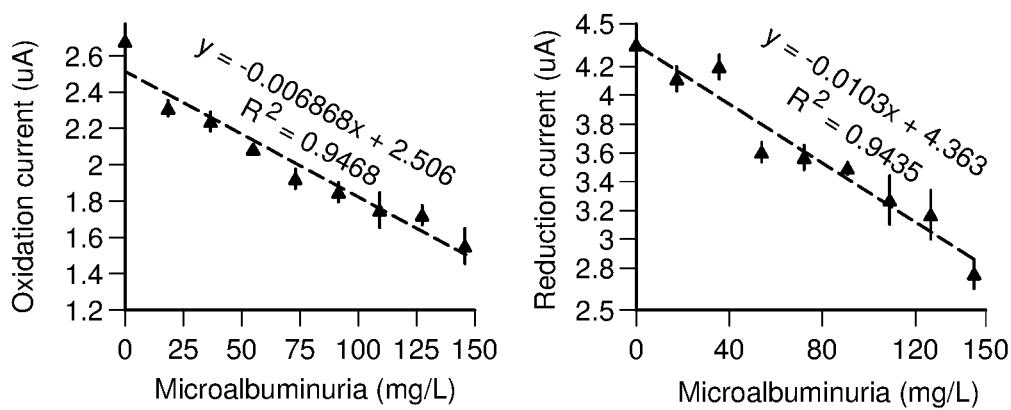

The albumin content in the urine sample binds Cu (II) thereby demonstrating a linear decrease in peak redox current with urine albumin concentration as shown in FIG. 23 (a) and FIG. 23(b). If the concentration of albumin in urine sample is increased then the albumin increasingly binds with Cu(II) thereby reducing the free Cu(II) concentration on the electrode resulting in the decrease in peak reduction current of free Cu(II).

The values of concentrations of the urine albumin (mg/L) along with corresponding reduction current values (µA) are recorded and tabulated as shown in Table 2. Table 2 can be prepared from linear fit equation as given below:

$$y=-0.0103x+4.363$$

In the above equation "y" represents the redox current value and "x" represents the concentration of analyte.

TABLE 2

| Urine Albumin Concentration (mg/L) | Reduction current (µA) |
| --- | --- |
| 0 | 4.35 |
| 18.2 | 4.12 |
| 36.4 | 4.20 |
| 54.6 | 3.60 |
| 72.8 | 3.57 |
| 91 | 3.50 |
| 109.2 | 3.27 |
| 127.4 | 3.17 |
| 145.6 | 2.74 |

Example 4: Copper Based Direct Detection of Urine Albumin in Synthetic Urine

A sample volume of synthetic urine of 220 uL is placed on the electrode having the $CuCl_2$ receptor of 2 to 6 µg then the peak redox current value is noted from cyclic voltammogram specifying a potential window from 0.6 V to −0.4 V in CHI Electrochemical workstation. The value of peak reduction current is 4.17 µA. This current value is searched in the Table 2 and the corresponding concentration of urine albumin thus obtained is 18.2 mg/L.

Example 5: Determination of Values of Urine Albumin Concentration and Corresponding Reduction Current Using MB-Hemin as a Receptor Synthetic urine is prepared by dissolving 14.1 g of NaCl, 2.8 g KCl, 17.3 g of urea, 19 ml ammonia water (25%), 0.60 g $CaCl_2$ and 0.43 g $MgSO_4$ in 0.02 mole/L of HCl. The final pH of synthetic urine is adjusted to 6.04 with using HCl and ammonia water. MB is dissolved in DI water. 10 to 45 mg of MB is dissolved in 10 ml DI water. 1 to 10 mg hemin dissolved in 40 ml synthetic urine. The 9 µL (5 µL hemin plus 4 µL MB) volume of this solution is used as a receptor for urine albumin detection. 3 mg of human albumin is dissolved in 10 ml of synthetic urine solution to prepare the micro albumin solution. 94 micro drop of receptor is premixed with the micro albumin solution with known concentrations and make the final volume 300 µL.

In the above equation "y" represents the redox current value and "x" represents the concentration of analyte.

Figure 24A:
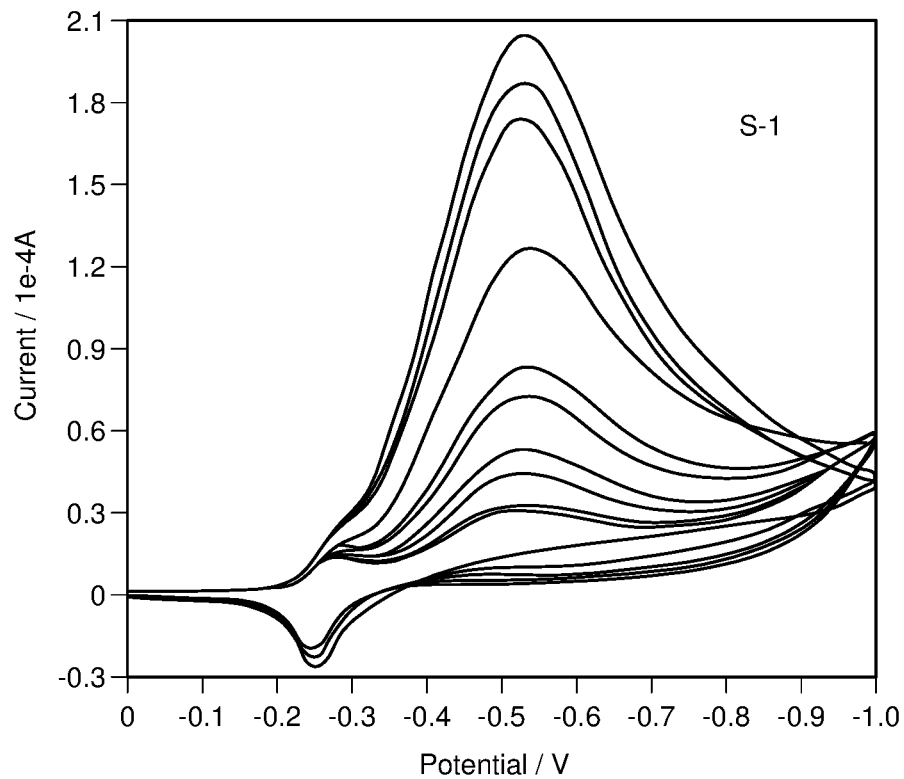
FIG. 24(a) is cyclic voltammogram of free hemin and MB with different urine albumin concentrations.

A desired volume of the biological sample (urine) is taken and dispensed on the electrode of the biosensor device and the corresponding cyclic voltammogram is obtained by using the CHI Electrochemical workstation using the potential window varies from 0 V to −1 V with scan rate of 0.1 V/sec, as shown in FIG. 24(a).

Figure 24B:
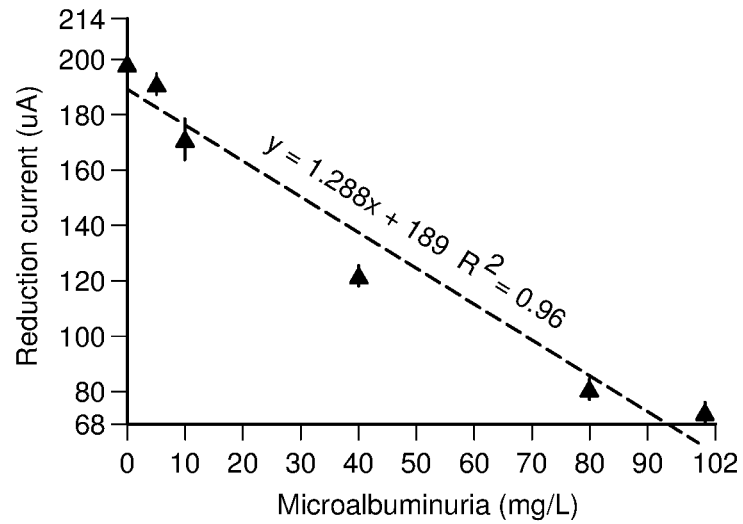
FIG. 24(b) depicts reduction current plot versus urine albumin concentration

Due to the catalytic current because of electron donation by LMB to hemin, we get the higher peak current even at lower concentration of hemin in comparison to the direct hemin based urine albumin detection, as described earlier. The albumin content in the urine sample binds hemin thereby demonstrating a linear decrease in peak redox current with urine albumin concentration as shown in FIG. 24(a) and FIG. 24(b). If the concentration of albumin in urine sample is increased then the albumin increasingly binds with hemin thereby reducing the free hemin concentration on the electrode resulting in the decrease in peak redox current of free hemin.

The values of concentrations of the urine albumin (mg/L) along with corresponding reduction current values (µA) are recorded and tabulated as shown in Table 3. Table 3 can be prepared from linear fit equation as given below:

$y = -1.288x + 189$

In the above equation "y" represents the redox current value and "x" represents the concentration of analyte.

TABLE 3

| Urine Albumin Concentration (mg/L) | Reduction current (µA) |
|---|---|
| 0 | 203.8 |
| 5 | 188.2 |
| 10 | 173.2 |
| 40 | 118 |
| 80 | 80.1 |
| 100 | 71.8 |
| 150 | 49.5 |

Example 6: MB-Hemin Based Direct Detection of Urine Albumin in Synthetic Urine

A sample volume of synthetic urine of 300 µL is placed on the electrode having the MB-hemin receptor of 5 to 15 µg MB plus 0.1 To 1 µg hemin then the peak redox current value is noted from cyclic voltammogram specifying a potential window from 0.6 V to −0.4 V in CHI Electrochemical workstation. The value of peak reduction current is 187.9 µA. This current value is searched in the Table 3 and the corresponding concentration of urine albumin thus obtained is 5 mg/L.

Example 7: Determination of Values of Urine Albumin Concentration and Corresponding Reduction Current Using MB-CuCl₂ as a Receptor Synthetic urine is prepared by dissolving 14.1 g of NaCl, 2.8 g KCl, 17.3 g of urea, 19 ml ammonia water (25%), 0.60 g $CaCl_2$ and 0.43 g $MgSO_4$ in 0.02 mole/L of HCl. The final pH of synthetic urine is adjusted to 6.04 with using HCl and ammonia water. 1 to 10 mg MB dissolved in 10 ml synthetic urine. 5 to 35 mg $CuCl_2$ is dissolved in 30 ml synthetic urine. (for example 40 µL $CuCl_2$ plus 30 µL MB) for urine albumin detection. 2 mg of human albumin is dissolved in 10 ml of synthetic urine solution to prepare the micro albumin solution. 70 µL drop of receptor is premixed with the micro albumin solution with known concentrations and make the final volume 220 µL.

Figure 25A:
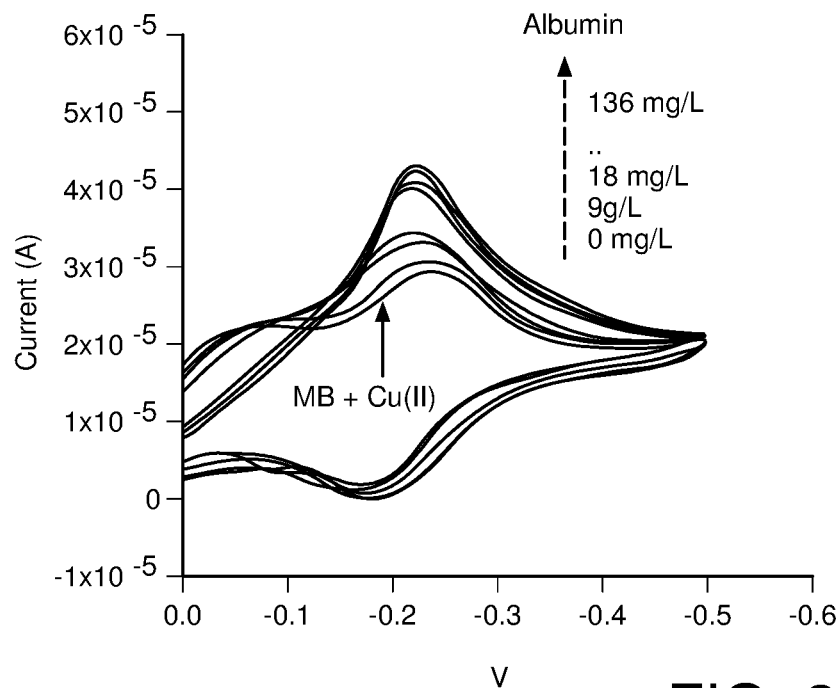
FIG. 25(a) depicts cyclic voltammogram of free Cu(II) in $CuCl_2$ and MB with different urine albumin concentrations.
Figure 25B:
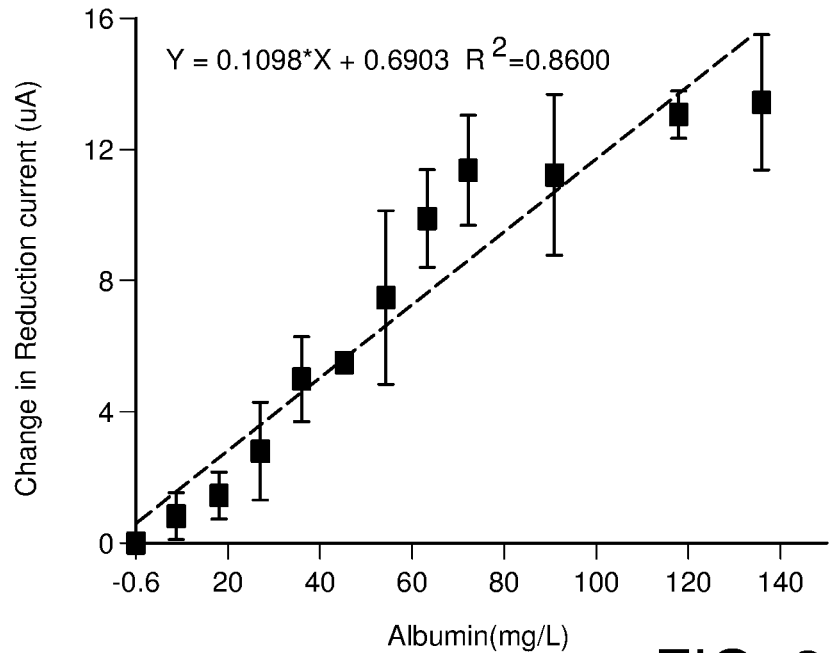
FIG. 25(b) depicts reduction current plot versus urine albumin concentration

A desired volume of the biological sample (urine) is taken and dispensed on the electrode of the biosensor device and the corresponding cyclic voltammogram is obtained by using the CHI Electrochemical workstation using the potential window varies from 0 V to −0.5 V with scan rate of 0.1 V/sec, as shown in FIG. 25 (a).

The albumin content in the urine sample binds cu (II) and form the albumin-copper complex. This complex increases the peck reduction current of methylene blue, thereby demonstrating a linear increase in peak reduction current with urine albumin concentration as shown in FIG. 25 (a) and FIG. 25 (b). If the concentration of albumin in urine sample is increased then the albumin increasingly binds with Cu (II) and will form the albumin-copper complex thereby oxidizing the more methylene blue concentration on the electrode resulting in the increase in peak reduction current of methylene blue.

The values of concentrations of the urine albumin (mg/L) along with corresponding reduction current values (µA) are recorded and tabulated as shown in Table 4. Table 4 can be prepared from linear fit equation as given below:

$y = 0.1098 + 0.6903$

In the above equation "y" represents the redox current value and "x" represents the concentration of analyte.

TABLE 4

| Urine Albumin Concentration (mg/L) | Reduction current (µA) |
|---|---|
| 0 | 29 |
| 9.09 | 31 |
| 18.18 | 31.4 |
| 27.27 | 32.2 |
| 36.36 | 33.1 |
| 45.45 | 34.6 |
| 54.54 | 40.2 |
| 63.63 | 40.7 |
| 72.72 | 40.9 |
| 90.9 | 43.1 |
| 118.17 | 42.5 |
| 136.35 | 45.1 |

Example 8: MB-CuCl₂ Based Direct Detection of Urine Albumin in Synthetic Urine

A sample volume of synthetic urine of 220 µL is placed on the electrode having the MB-$CuCl_2$ receptor of 10 to 50 µg MB plus 5 to 55 µg $CuCl_2$ then the peak redox current value is noted from cyclic voltammogram specifying a potential window from 0 V to −0.5 V in CHI Electrochemical workstation. The value of peak reduction current is 30.8 µA. This current value is searched in the Table 4 and the corresponding concentration of urine albumin thus obtained is 9.09 mg/L.

Example 9: Determination of Values of Human Serum Albumin in Blood Plasma Sample Concentration and Corresponding Reduction Current Using CuCl$_2$ as a Receptor Human blood plasma is with albumin concentration 34.02 g/L is taken as master solution. The plasma is diluted to get the concentrations of albumin from 5 g/l to 32.09 g/l. A stock solution of CuCl$_2$ receptor is prepared in saline water with 70 to 150 g/L of concentrations. and 20 µL micro drop is premixed with diluted plasma solution and 300 µL total volume is placed on to the electrode surface and the peak reduction current value is measured.

A desired volume of the human blood plasma is taken and dispensed on the electrode of the biosensor device and the corresponding cyclic voltammogram is obtained by using the CHI Electrochemical workstation using the potential window varies from 1 V to −0.6 V with scan rate of 0.3 V/sec as shown in FIG. 26 (a).

Figure 26A:
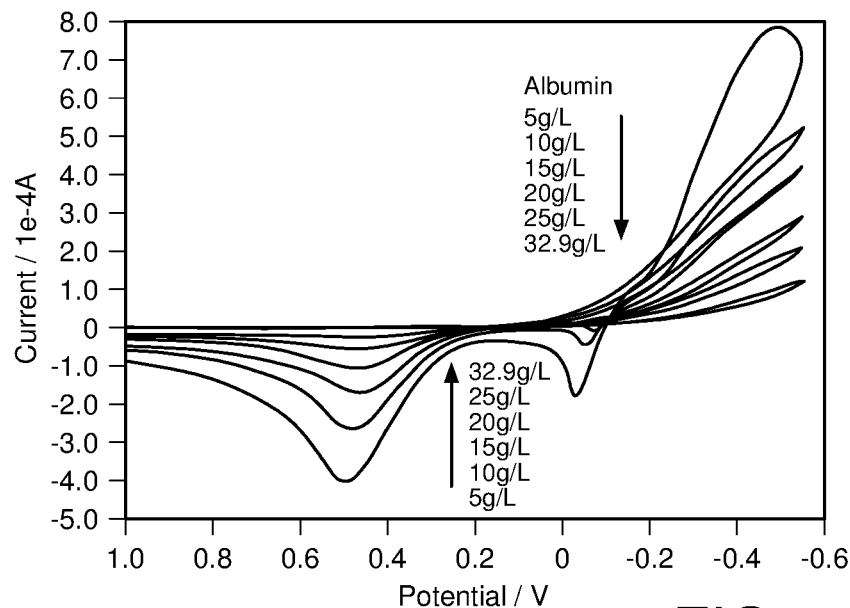
FIG. 26(a) is a cyclic voltammogram of free Cu(II) in $CuCl_2$ with different concentrations of albumin in human blood plasma.
Figure 26B:
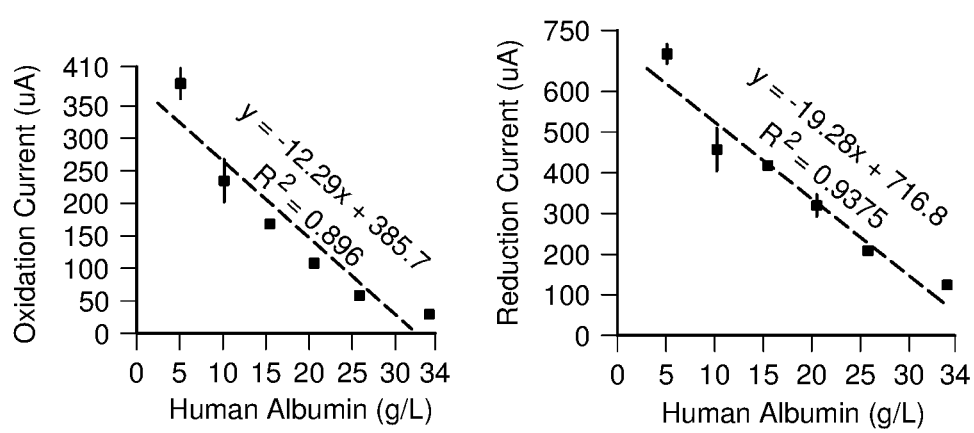
FIG. 26(b) depicts reduction and oxidation currents plot versus urine albumin concentration

The albumin content in the human plasma sample binds Cu(II) thereby demonstrating a linear decrease in peak redox current with urine albumin concentration as shown in FIG. 26(a) and FIG. 26(b). If the concentration of albumin in plasma sample is increased then the albumin increasingly binds with Cu(II) thereby reducing the free Cu(II) concentration on the electrode resulting in the decrease in peak reduction current of free Cu(II).

The values of concentrations of the human blood plasma albumin (g/L) along with corresponding reduction current values (µA) are recorded and tabulated as shown in Table 5. Table 5 can be prepared from linear fit equation as given below:

$$y=-19.28x+716.8$$

In the above equation "y" represents the redox current value and "x" represents the concentration of analyte.

TABLE 5

| Human Plasma Albumin Concentration (g/L) | Reduction current (µA) |
|---|---|
| 5 | 686.6 |
| 10 | 440.9 |
| 15 | 418 |
| 20 | 333 |
| 25 | 208 |
| 32.9 | 122.1 |

Example 10: CuCl$_2$ Based Direct Detection of Albumin in Human Blood Plasma

A sample volume of synthetic urine of 300 µL is placed on the electrode having the CuCl$_2$ receptor of 1 to 10 mg CuCl$_2$ then the peak redox current value is noted from cyclic voltammogram specifying a potential window from 1 V to −0.6 V in CHI Electrochemical workstation. The value of peak reduction current is 676.8 µA. This current value is searched in the Table 5 and the corresponding concentration of urine albumin thus obtained is 5 g/L.

Example 11: Determination of Values for Methemealbumin in Biological Sample and Corresponding Reduction Current Using Methylene Blue as a Receptor Methemalbumin is prepared by known methods by dissolving hemin (Sigma Aldrich) alkali solution. This solution is mixed with 5 ml of 2% human albumin and the pH is adjusted to 7.4 with 1 N HCl. 1 to 7 mg of MB is dissolved in 10 ml of PBS at pH7. Different concentration of methemalbumin solution is added in the MB solution, in order to get the peak reduction current values. The peak reduction current values using the CHI Electrochemical workstation using the potential window varies from −0.2 V to −0.5 V with scan rate of 0.1 V/sec. The volume of the methemalbumin along with corresponding reduction current values (µA) are recorded and tabulated as shown in Table 6. Table 6 can be prepared from linear fit equation as given below:

$$y=1.006x+41.19$$

In the above equation "y" represents the redox current value and "x" represents the concentration of analyte.

TABLE 6

| Volume of methemalbumin complex (µL) | Reduction current (µA) |
|---|---|
| 0 | 32 |
| 10 | 54 |
| 20 | 69 |
| 30 | 78 |
| 40 | 80 |
| 50 | 85 |

A desired volume (µL) of the receptor MB is dispensed on the electrode surface of the biosensor device and dried.

Figure 27A:
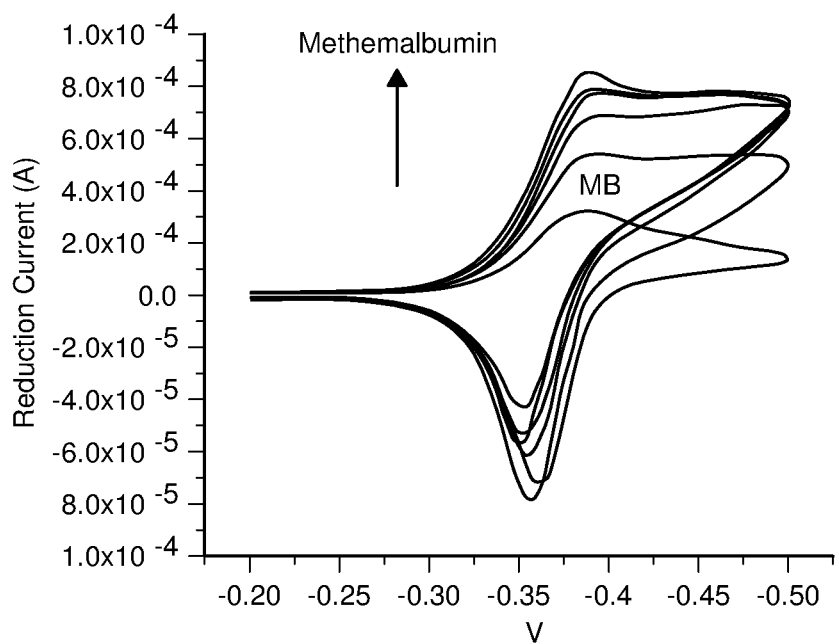
FIG. 27(a) depicts cyclic voltammogram of MB with different methemalbumin concentrations.
Figure 27B:
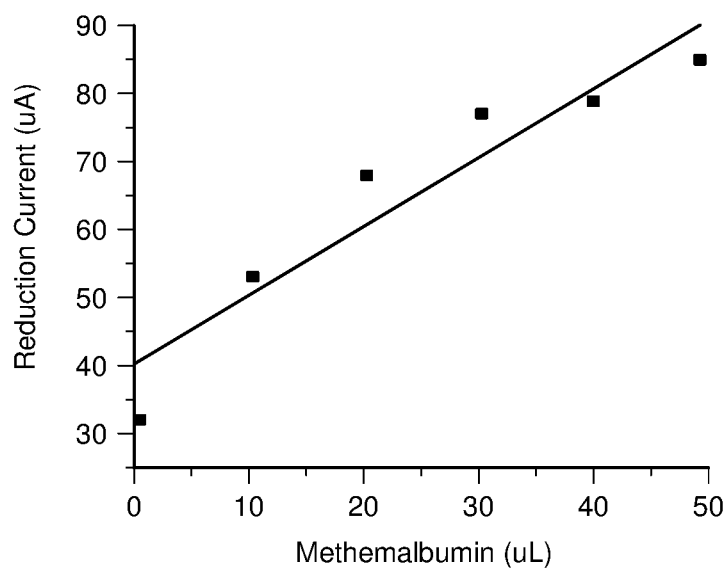
FIG. 27(b) is a plot showing reduction current versus methemalbumin concentrations.

A desired volume of the biological sample (methemealbumin complex in standard solution) is taken and dispensed on the electrode of the biosensor device and the corresponding cyclic voltammogram is obtained by using CHI-Electrochemical Workstation using the potential window from −0.2 V to −0.5V lith scan rate of 0.1.V/sec, as shown in FIG. 27 (a) and FIG. 27 (b).

The reduced form of MB (LMB) donates its electrons to the methemalbumin complex thereby demonstrating a linear increase in peak reduction current with methemalbumin complex as shown in FIG. 27 (a) and FIG. 27 (b).

Advantages of the Present Invention

In the present invention non-enzymatic and non-antibody based receptors are used in conjunction with electrodes, for quantitative measurement bioanalytes viz., urine albumin, HSA, methemalbumin and GA in a biological sample.

The present invention adopts a method of the doping of human albumin with electrochemically active substance for the electrochemical detection of bioanalytes related to human albumin.

In the quantitative measurement of bioanalytes of the present invention a minimal invasive technique where a reduced volume of sample volume is used.

It is also understood that the following claims are intended to cover all the generic and specific features of the invention herein described and all statements of the scope of the invention, which as a matter of language might be said to fall there between.

We claim:

1. An electrochemically active device for collecting and retaining a biological sample, comprising:
   (i) at least a pair of conductive tracks disposed on a substrate;
   (ii) at least one electrode member, said member comprising two or three electrodes connected to said conductive tracks; and (iii) an electrochemically active receptor, wherein said receptor is selected from the group consisting of:
   a) a metal porphyrin,
   b) a combination of a metal porphyrin and methylene blue,
   c) a copper (II) salt, and
   d) a combination of a copper (II) salt and methylene blue,
and wherein said receptor is in chemical contact with said at least one electrode member and a biological sample with a bioanalyte,
wherein a membrane is disposed on said at least one electrode member; and
said membrane is treated with a boronate affinity agent, selected from the group consisting of boronic acid, phenyl boronic acid (PBA), and aminophenyl boronic acid (APBA).

2. The device as claimed in claim 1, wherein said substrate comprises a polymer or paper.

3. The device as claimed in claim 1, wherein the at least one electrode member comprises three electrodes disposed on said substrate.

4. The device as claimed in claim 1, comprising a plurality of electrode members comprising two electrodes disposed on said substrate.

5. The device as claimed in claim 1, comprising a plurality of electrode members comprising three electrodes disposed on said substrate.

6. The device as claimed in claim 1, wherein said at least one electrode member comprises patterned electrodes.

7. The device as claimed in claim 1, wherein said device is disposed in a housing, wherein said housing is a cartridge or a cassette.

8. A system comprising an electrochemically active device, and a holder, said system comprising:
   (i) a device detection and signal conditioning means disposed in a housing;
   (ii) a USB connector disposed at one end of said housing and an electrically conductive port disposed at the other end of said housing; and
   (iii) an electrochemically active device for collecting and retaining a biological sample, said electrochemically active device disposed to connect to said housing through said electrically conductive port, said electrochemically active device comprising:
      a) at least a pair of conductive tracks,
      b) at least one electrode member, said at least one electrode member comprising two or three electrodes,
      c) a membrane disposed on said at least one electrode member, said membrane comprising boronate affinity agent selected from the group consisting of boronic acid, phenyl boronic acid (PBA), and aminophenyl boronic acid (APBA), and
      d) an electrochemically active receptor, wherein said receptor is selected from the group consisting of:
         a) a metal porphyrin,
         b) a combination of a metal porphyrin and methylene blue,
         c) a copper (II) salt, and
         d) a combination of a copper (II) salt and methylene blue,
      wherein said receptor is in chemical contact with said at least one electrode member.

9. A point-of-care biosensor for measuring a concentration of a bioanalyte in a biological sample, the biosensor comprising:
   (i) a housing having a display member and an electrically conducting port,
   (ii) an electrochemically-active device disposed to connect to said housing through said electrically conductive port for collecting and retaining a biological sample, wherein said device comprises:
      1) at least a pair of conductive tracks,
      2) at least one electrode member, said member comprising two or three electrodes,
      3) a membrane disposed on said at least one electrode member, said membrane treated with a boronate affinity agent selected from the group consisting of boronic acid, phenyl boronic acid (PBA), aminophenyl boronic acid (APBA),
      4) an electrochemically active receptor, wherein said receptor is selected from the group consisting of:
         a) a metal porphyrin,
         b) a combination of a metal porphyrin and methylene blue,
         c) a copper (II) salt, and
         d) a combination of a copper (II) salt and methylene blue, and
      wherein said receptor in chemical contact with said at least one electrode member; and
   (iii) a digital controller disposed in said housing and configured to measure redox current from a redox potential applied to said device, retrieve and display bioanalyte concentration, by linearly matching the concentrations of bioanalyte.

10. A method for measuring a concentration of a bioanalyte in a biological sample, comprising the steps of:
   (i) receiving a volume of a biological sample on a device, said device comprising:
      a) at least a pair of conductive tracks disposed on a substrate,
      b) at least one electrode member, said member comprising two or three electrodes connected to said conductive tracks,
      c) an electrochemically active receptor, wherein said receptor is a metal porphyrin, a combination of a metal porphyrin and methylene blue, a copper (II) salt, or a combination of a copper (II) salt and methylene blue, and
      wherein said receptor is in chemical contact with said at least one electrode member;
      d) a membrane disposed on said at least one electrode member, said membrane treated with a boronate affinity agent selected from the group consisting of boronic acid, phenyl boronic acid (PBA), aminophenyl boronic acid (APBA),
   (ii) applying a redox potential to said at least one electrode member and measuring the corresponding redox current;
   (iii) determining the concentration of bioanalyte in said biological sample by linearly matching said redox current to the concentration of bioanalyte.

11. The method as claimed in claim 10, wherein said biological sample comprises human blood and urine.

12. The method as claimed in claim 10, wherein said volume is in the range of 1-300 microlitres (µL).

13. The method as claimed in claim 10, wherein said bioanalyte comprises urine albumin, human serum albumin (HSA), or glycated albumin (GA).

14. The method as claimed in claim 13, wherein the bioanalyte is glycated albumin, said glycated albumin measured by (i) receiving a biological sample with albumin on a device, said device comprising:
  a) at least two sets of two-electrode members, wherein one of said at least two sets of two-electrode members comprises a boronic acid membrane to filter glycated albumin, wherein said boronic acid membrane is treated with a boronate affinity agent selected from the group consisting of boronic acid, phenylboronic acid (PBA), and aminophenyl boronic acid (APBA); and
  b) an electrochemically active receptor, wherein said receptor is a metal porphyrin, a combination of a metal porphyrin and methylene blue, a copper (II) salt, or a combination of a copper (II) salt and methylene blue,
    wherein said receptor is in chemical contact with said at least two sets of two-electrode members;
(ii) applying an identical redox potential to said two sets of two-electrode members and determining the two sets of concentrations of albumin from said two sets of two electrode members by measuring the corresponding redox currents, wherein one set of said two electrode members measures concentration of total albumin by measuring total redox current and said other set of two electrode members measures concentration of non-glycated albumin by measuring non-glycated redox current due the filtration of glycated albumin by the boronic acid membrane;
(iii) obtaining the percentage glycated redox current by subtracting said total redox current from said non-glycated redox current, and dividing the resultant current by said total redox current to get percentage glycated redox current; and
(iv) determining the percentage glycated albumin by linearly matching said percentage glycated redox current with the values of percentage glycated albumin.

15. The method as claimed in claim 14, wherein said receptor is selected from the group consisting of metal porphyrin substances and copper (II) salts.

* * * * *